(12) United States Patent
Campisi et al.

(10) Patent No.: US 6,409,648 B1
(45) Date of Patent: Jun. 25, 2002

(54) POLYNUCLEOTIDES ENCODING TRF1 BINDING PROTEINS

(75) Inventors: Judith Campisi, Berkeley; Sahn-Ho Kim, Albany, both of CA (US)

(73) Assignee: The Regents of the University of California, Oakland, CA (US)

( * ) Notice: Subject to any disclaimer, the term of this patent is extended or adjusted under 35 U.S.C. 154(b) by 37 days.

(21) Appl. No.: 09/608,917

(22) Filed: Jun. 30, 2000

Related U.S. Application Data

(60) Provisional application No. 60/142,191, filed on Jul. 1, 1999.

(51) Int. Cl.[7] .................. C07H 21/02; C07H 21/04; C12N 1/21; C12N 15/63; C12P 21/00
(52) U.S. Cl. .................. 535/69.1; 435/71.1; 435/252.3; 435/320.1; 435/471; 536/23.1; 536/23.5; 536/24.31; 536/24.33
(58) Field of Search ............................ 536/23.1, 23.5, 536/24.31, 24.33; 435/320.1, 71.1, 69.1, 471, 252.3

(56) References Cited

U.S. PATENT DOCUMENTS

| | | |
|---|---|---|
| 5,707,795 A | 1/1998 | West et al. |
| 5,733,730 A | 3/1998 | De Lange |
| 5,747,317 A | 5/1998 | Cao |
| 5,760,062 A | 6/1998 | Gaeta et al. |
| 5,767,278 A | 6/1998 | Gaeta et al. |
| 5,770,422 A | 6/1998 | Collins |
| 5,770,613 A | 6/1998 | Gaeta et al. |
| 5,846,723 A | 12/1998 | Kim et al. |
| 5,858,777 A | 1/1999 | Villeponteau et al. |
| 5,859,183 A | 1/1999 | De Lange et al. |
| 5,863,726 A | 1/1999 | Harley et al. |
| 5,863,936 A | 1/1999 | Gaeta et al. |
| 5,888,747 A | 3/1999 | Cao |

OTHER PUBLICATIONS

Marra et al., NCBI Database, National Center for Biotechnology Information, NIH (Bethesda, MD, USA). GenBank Accession No. W70730, Jun. 17, 1996.*

Marra et al. NCBI Database, National Center for Biotechnology Information, NIH (Bethesda, MD, USA). GenBank Accession No. W91321. Sep. 12, 1996.*

Matsubara et al. N–Geneseq Database. Accession No. AAT26298. Oct. 10, 1996.*

Allsopp et al., "Telomere Length Predicts Replicative Capacity of Human Fibroblasts," Proc. Natl. Acad. Sci. USA 89:10114–10118 (1992).

B. Rensberger Washington Post, p. A1, A12. Cancer's Immortality may Depend on Enzyme. Apr. 12, 1994.

Baird et al., "Mechanism Underlying Telomere Repeat Turnover Revealed by Hypervariable Variant Repeat Distribution Patterns in the Human Xp/Yp Telomere" EMBO J.14:5433–5443 (1995).

Barany, Genetic Disease and DNA Amplifications Using Closed Thermostable Ligase, Proc. Natl. Acad. Sci. USA, 88:189–193 (1991).

(List continued on next page.)

Primary Examiner—Carla J. Myers
(74) Attorney, Agent, or Firm—David J. Aston; Thomas Brody; Michelle S. Chew

(57) ABSTRACT

The present invention provides a novel telomere associated protein (Trf1-interacting nuclear protein 2 "Tin2") that hinders the binding of Trf1 to its specific telomere repeat sequence and mediates the formation of a Tin2-Trf1-telomeric DNA complex that limits telomerase access to the telomere. Also included are the corresponding nucleic acids that encode the Tin2 of the present invention, as well as mutants of Tin2. Methods of making, purifying and using Tin2 of the present invention are described. In addition, drug screening assays to identify drugs that mimic and/or complement the effect of Tin2 are presented.

10 Claims, 5 Drawing Sheets

OTHER PUBLICATIONS

Blackburn, Telomerases, Ann. Rev. Biochem. 61:113–129 (1992).

Blackburn et al., Recognition and Elongation of Telemeres by Telomerase, Genome, 31:553–560 (1989).

Blackburn, "The Molecular Structure of Centromeres and Telemeres" Annual Reviews in Biochemistry 53:163 (1984).

Blackburn, Structure and Function of Telomeres, Nature, 350:569–573 (May 1991).

C.W. Greider, Cold Spring Harbor Symposia on Quantitative Biology, vol. LVIII, Cold Spring Harbor Laboratory, NY. Telomerase and Telomere–length Regulation: Lessons from Small Eukaryotes to Mammals (1993).

Cech, "Ribozymes and Their Medical Implications" JAMA, 260:3030 (1988).

Cooke and Smith, "Variability at the Telomeres of the Human X/Y Pseudoautosomal Region" CSHSQB LI:213 (1986).

Cotten, "The In Vivo Application of Ribosomes," Trends in Biotechnology 8:174–178 (1990).

Counter et al., Telomere shortening associated with chromosome instability is arrested in immortal cells which express telomerase activity, EMBO J. 11(5):1921–1929 (1992).

Counter et al., Stabilization of Short Telomeres and Telomerase Activity Accompany Immortalization of Epstein–Barr Virus–Transformed Human B Lymphocytes, Journal of Virology, 68(5):3410–3414 (1994).

Counter et al., Telomerase Activity in Human Ovarian Carcinoma, Proc. Natl. Acad. Sci., 91:2900–2904 (1994).

Counter et al., Telomerase Activity in Normal Leukocytes and in Hematologiic Malignancies, Blood, 85(9):2315–2320 (1995).

Czech (1988), Ribozymes and their medical implications, JAMA 260(20):3030–3034 (1988).

Eck and Nabel, Antisense oligonucleotides for therapeutic intervention, Current Opinions Biotechnology 2:897–904 (1991).

Feng. J., et al., "The RNA Component of Human Telomerase", Science 269:1236 1241 (1995).

Gall, "Tying Up Loose Ends" Nature 344:108 (1990).

Goldstein, "Replicative Senescence: The Human Fibroblast Comes of Age" Science 249:1129 (1990).

Gottschling et al., "Position Effect at S. cerevisiae Telomeres: Reversible Repression of Pol II Transcription" Cell 63:751 (1990).

Gray et al., "Cloning and Expression of Genes for the Oxytricha Telomere–binding Protein Specific Subunit Interactions in the Telomeric Complex" Cell 67:807 (1991).

Greider, Telomerase is processive, Mol. Cell. Bio. 11:4572–4580 (1991).

Greider and Blackburn, A telomeric sequence in the RNA of Tetrahymena telomerase required for telomere repeat synthesis, Nature 337(6205):331–337 (1989).

Greider and Blackburn, The Telomere Terminal Transferase of Tetrahymena Is a Ribonucleoprotein Enzyme with Two Kinds of Primer Specificity, Cell, 51:887–898 (1987).

Greider et al., A Telomeric Sequence in the RNA of Tetrahymena Telomerase Required for Telomere Repeat Synthesis, Nature, 337:331–337 (1989).

Greider et al., Identification of a Specific Telomere Terminal Transferase Activity in Tetrahymena Extracts, Cell, 43:405–413 (1985).

Greider, "Telomeres, Telomerase and Senescence" Bioessays 12:63 (1990).

Greider, "Chromosome First Aid" Cell 67:645 (1991).

Ham and McKeehan, "Media and Growth Requirements-"Methods in Enzymology LVIII:44 (1979).

Harley et al. Telomere Loss: Mitotic Clock or Genetic Time Bomb?, Mutation Research, 256:271–282 (1991).

Harley et al., "The Telomere Hypothesis of Cellular Aging," Experimental Gerontology 27:375–382 (1992).

Harley et al., Telomeres Shorten During Ageing of Human Fibroblasts, Nature, 345:458–460 (1990).

Harrington and Greider, "Telomerase Primer Specificity and Chromosome Healing" Nature 353:451 (1991).

Hayflick and Moorhead, "The Serial Cultivation of Human Diploid Cell Strains" Experimental Cell Research 25:585 (1961).

Henderson et al., "Telomere G–strand Structure and Function Analyzed by Chemical Protection, Base Analogue Substitution, and Utilization by Telomerase In Vitro" Biochemistry 29:732 (1990).

Hiyama et al., Length of Telomeric Repeats in Neuroblastoma: Correlation with Prognosis and Other Biological Characteristics, Jpn. J. Cancer Res., 83:159–164 (1992).

Ijdo et al., "Improved Telomere Detection Using a Telomere Repeat Probe $(TTAGGG)_n$ Generated by PCR" Nucleic Acids Research 19:4780 (1991).

Innis et al. In PCR Protocols: A Guide to Methods and Applications, Ch. 1, 2 and 3 (1990).

J. Rennie, Scientific American, Jul. pp. 14–16, Immortal's Enzyme (1994).

Jankovic et al., "Telomere Loss and Cancer" Nature 350:197 (1990).

Kim et al., Specific Association of Human Telomerase Activity with Immortal Cells and Cancer, Science, 266:2011–2015 (1994).

Klingelhutz et al., "Restoration of Telomeres in Human Papoillomavirus–Immortalized Human Anogenital Tpithelial Cells," Molecular and Cellular Biology 14:961–969 (1994).

Kwoh et al., "Transcription Based Amplification System and Detection of Amplified Human Immunodeficiency Virus Type 1 with a Bead–Based Sandwich Hybridization Format" Proc. Natl. Acad. Sci. USA 86:1173–1177 (1989).

Lingner et al., Telomerase RNAs of different ciliates have a common secondary structure and a permuted template, Genes and Development 8:1989–1998 (1984).

Lundblad and Szostak, "A Mutant With a Defect in Telomere Elogation Leads to Senescence in Yeast" Cell 57:633 (1989).

Mehle et al., "Telomere shortening in renal cell carcinoma," Cancer Research, 54 (1) 236 41 (1994).

Morin, The human telomere terminal transferase enzyme is a ribonucleoprotein that synthesizes TTAGGG Repeats, Cell, 59:521–529 (1989).

Morin, Recognition of a chromosome truncation site associated with alpha–thalassaemia by human telomerase, Nature 353:454–456 (1991).

Muller et al., "New Telomere Formation After Developmentally Regulated Chromosomal Breakage During the Process of Chromosome Diminution in Ascaris lumbricoides" Cell 67:815 (1991).

Ohno, "Strict Relationship Between Dialyzed Serum Concentration and Cellular Life Span In Vitro" Mechanisms of Aging and Development 11:179(1979).

Olovnikov "A Theory of Marginotomy" J. Theoretical Biology 41:181 (1973).

P. Nilsson et al.,Oncogene 9:3043–3048. Telomerase activity in vivo in human malignant hematopoietic cells (1994).

Prowse, Karen R., et al, Identification of a nonprocessive telomearse activity from mouse cells, Proc. Natl. Acad. Aci. USA 90:1493–1497 (1993).

Romero and Blackburn, A conserved secondary structure for telomerase RNA, Cell 67:343–353 (1991).

Shay et al, Loss of Telomeric DNA During Aging may Predispose Cells to Cancer, International Journal of Oncology, 3:559–563 (1993).

Shipen–Lentz and Blackburn, Functional evidence for an RNA template in telomerase, Science 247:546–552 (1990).

Singer and Gottschling (1994), TLC1: Template RNA Component of *Saccharomyces cerevisiae* Telomerase, Science 266:404–409.

Smith and Whitney, "Intraclonal Variation in Proliferative Potential of Human Diploid Fibroblastsistochastic Mechanisms for Cellular Aging" Science 207:82 (1980).

Starling et al., "Extensive Telomere Repeat Arrays in Mouse are Hypervariable" Nucleic Acids Research 18:6881 (1990).

Strahl and Blackburn, "The Effects of Nucleoside Analogs on Telomerase and Telomeres in Tetrahymena" Nucleic Acids Research 22:893–900 (1994).

Szostak, "The Beginning of the Ends" Nature 337:303 (1989).

T. de Lange, "Telomerase Activity in Human Tumors", Tumor Telomeres; Telomeres, pp. 283–284 (1995).

Wang and Zaklen, "Telomere–Telomere Recombination Provides an Express Pathway for Telomere Acquisition" Nature 345:456 (1990).

Weber et al, "Characterization and Organization of DNA Sequences Adjacent to the Human Telomere Associated Repeat $(TTAGGG)_n$ " Nucleic Acids Research 18:3353–3361 (1990).

Wilkie et al., "A Truncated Human Chromosome 16 Associated with Alpha Thalassaemia is Stabilized by Addition of Telomeric Repeat $(TTAGGG)_n$ " Abstract, Nature 346(6287):868–871 (1990).

Windle and McGuire, Telomeres: The Long and the Short of It, Proceedings of the American Association for Cancer Research, Eighty–Third Annual Meeting of the American Association for Cancer Research, 33:594–595 (1992).

Yan, Riqiang, et al. "Amino Acid Sequence of the Human Protein Synthesis Initiation Factor elF–4.gamma.", Journal of Biological Chemistry 267(32):23226–23231 (1992).

Yu and Blackburn, Developmentally programmed healing of chromosomes by telomerase in Tetrahymena, Cell 67:823–832 (1991).

Yu, Guo–Liang, et al. "In vivo alteration of telomere sequences and senescence caused by mutated Tetrahymena RNAa", Nature 344:126–132 (1990).

Zahler et al., Inhibition of telomerase by G–quartet DNA structures, Nature 350:718–720 (1991).

* cited by examiner

FIGURE 1.
In the absence of Tin2-Trf1 complex, telomerase can access the telomere.
Due to the presence of Tin2-Trf1 complex, telomerase cannot access the telomere.
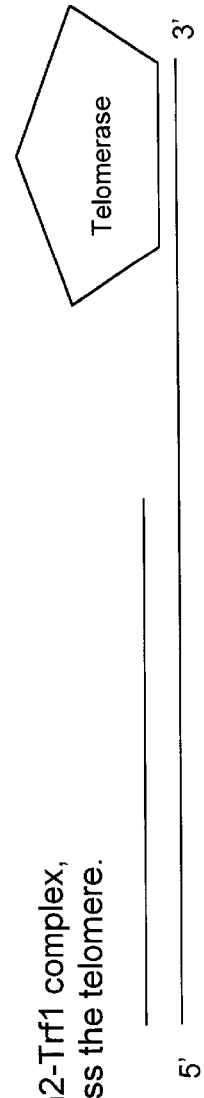
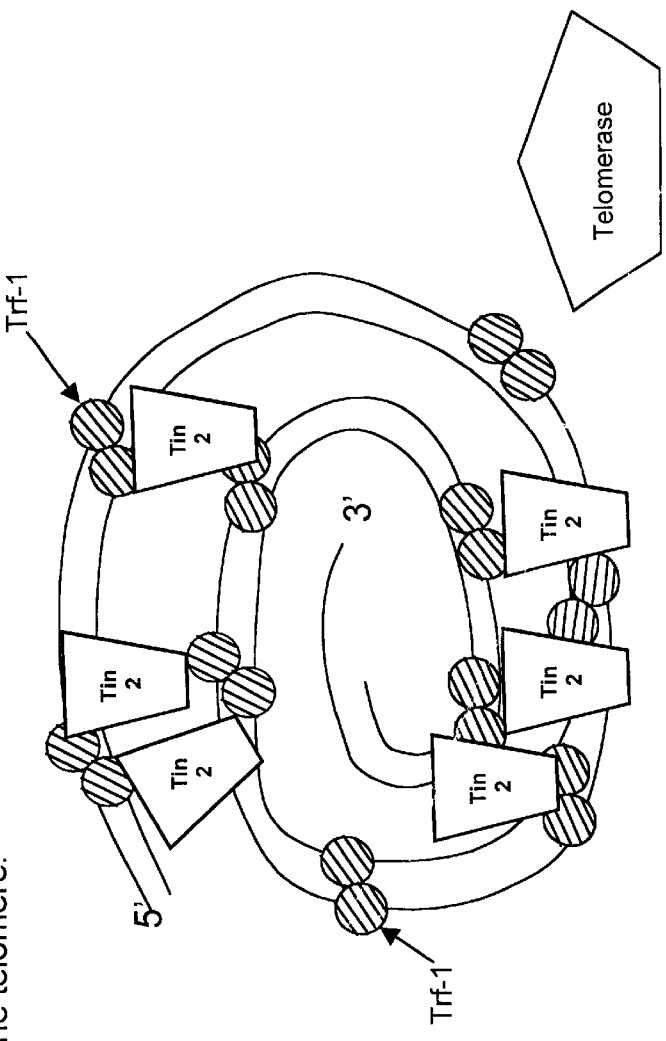

FIGURE 2. TIN-2

SEQUENCE LISTING

```
<160> NUMBER OF SEQ ID NOS:   4

<210> SEQ ID NO 1
<211> LENGTH: 2095
<212> TYPE: DNA
<213> ORGANISM: human

<400> SEQUENCE: 1
acgtttaaag ctgagcgacc cagtgccact ggagacggtc agcttctcca ctcaggctcc      60
tccagcccga gccagaagac cccctccccc ataattctgg gggccgatgg aagggagccg     120
agtcagatcg cgaggtaccc atagccgaca gaccggagcg acagggagtt gccataagcc     180
ccgcccctag gagtgatcgg aaagcctcac ccatccgggt gaggaacccg gagggaccgc     240
ctccgggcgg agcccgccga ccatggctac gcccctggtg gcgggtcccg cagctctacg     300
cttcgccgcc gcggctagct ggcaggttgt gcgcggacgc tgcgtggaac attttccgcg     360
agtactggag tttctgcgat ctctgcgcgc tgttgcccct ggcttggttc gctaccggca     420
ccacgaacgc ctttgtatgg gcctaaaggc caaggtggtg gtggagctga tcctgcaggg     480
ccggccttgg gcccaagtcc tgaaagccct gaatcaccac tttccagaat ctggacctat     540
```

-continued

```
agtgcgggat cccaaggcta caaagcagga tctgaggaag attttggagg cacaggaaac    600
tttttaccag caggtgaagc agctgtcaga ggctcctgtg gatttggcct cgaagctgca    660
ggaacttgaa caagagtatg gggaacccct tctggctgcc atggaaaagc tgcttttga    720 gtacttgtgt cagctggaga aagcactgcc tacaccgcag gcacagcagc ttcaggatgt    780
gctgagttgg atgcagcctg gagtctctat cacctcttct cttgcctgga gacaaatatgg   840 tgtggacatg gggtggctgc ttccagagtg ctctgttact gactcagtga acctggctga    900
gcccatggaa cagaatcctc ctcagcaaca aagactagca ctccacaatc ccctgccaaa    960
agccaagcct ggcacacatc ttcctcaggg accatcttca aggacgcacc cagaacctct    1020
agctggccga cacttcaatc tggcccctct aggccgacga agagttcagt cccaatgggc    1080
ctccactagg ggaggccata aggagcgccc cacagtcatg ctgtttccct ttaggaatct    1140
cggctcacca acccaggtca tatctaatcc tgagagcaag gaagaacatg cgatatacac    1200
agcagaccta gccatgggca aagagcacc ctccaatggg aagtataagg gtccatacca    1260
gaccctgggg ggaagggctc tgaaggagaa cccagttgac ttgcctgcca cagagcaaaa    1320
ggagtgagtg gaacagagtt gcttcttaat aggagcacat tctttgcctg ccttcccttc    1380
atcctatcct ctttgcttgc tctcacctca ggaattgctt ggattgatac atggacccc    1440 tgagactatc attattacct cctagggcca ggaagccagg taggtagtct gagtcaggat    1500
tggatcaaca gcctcctctc ttggggactc tcaagagcct gtgttcatct agaagtagta    1560
gtttgattct ggtttccctc atacagtgtg tcctccgtct ctgtgcagct ccgtcattac    1620 catagggac ttggttttag actctgatga ggaagaaaat ggccagggg aaggaaaggt     1680 gagtgggaag gagcagaaag ctgggaaagg ggatgggtag aacaagactg agaaatccac    1740
atgcttcaga attcagaggg ttcagggaat ggtttcggat agtaggctct ccctgctccc    1800
ttctatacag gaatctctgg aaaactatca gaagacaaag tttgacacct tgataccac    1860 tttttgtgaa tacctacccc cttctggcca cggtgccata cctgtttctt cctgtgactg    1920
tagaaacagt tctagacctt tgtgatagaa ctaaaatgct ctctgtactc tagtctcctg    1980
cctcctcagt tctgcaagta gtttagtagg aatgaagtgg aagtccaggc ttggattgcc    2040
taactacact gctaaaaata tttgtaatcc ttaataatta aactttggat ttgtt          2095
```

<210> SEQ ID NO 2
<211> LENGTH: 354
<212> TYPE: PRT
<213> ORGANISM: human

<400> SEQUENCE: 2

```
Met Ala Thr Pro Leu Val Ala Gly Pro Ala Ala Leu Arg Phe Ala Ala
1               5                   10                  15

Ala Ala Ser Trp Gln Val Val Arg Gly Arg Cys Val Glu His Phe Pro
            20                  25                  30

Arg Val Leu Glu Phe Leu Arg Ser Leu Arg Ala Val Ala Pro Gly Leu
        35                  40                  45

Val Arg Tyr Arg His His Glu Arg Leu Cys Met Gly Leu Lys Ala Lys
    50                  55                  60

Val Val Val Glu Leu Ile Leu Gln Gly Arg Pro Trp Ala Gln Val Leu
65                  70                  75                  80

Lys Ala Leu Asn His His Phe Pro Glu Ser Gly Pro Ile Val Arg Asp
                85                  90                  95

Pro Lys Ala Thr Lys Gln Asp Leu Arg Lys Ile Leu Glu Ala Gln Glu
```

-continued

```
                    100                 105                 110
Thr Phe Tyr Gln Gln Val Lys Gln Leu Ser Glu Ala Pro Val Asp Leu
            115                 120                 125
Ala Ser Lys Leu Gln Glu Leu Gln Glu Tyr Gly Glu Pro Phe Leu
        130                 135                 140
Ala Ala Met Glu Lys Leu Leu Phe Glu Tyr Leu Cys Gln Leu Glu Lys
145                 150                 155                 160
Ala Leu Pro Thr Pro Gln Ala Gln Leu Gln Asp Val Leu Ser Trp
            165                 170                 175
Met Gln Pro Gly Val Ser Ile Thr Ser Ser Leu Ala Trp Arg Gln Tyr
            180                 185                 190
Gly Val Asp Met Gly Trp Leu Leu Pro Glu Cys Ser Val Thr Asp Ser
        195                 200                 205
Val Asn Leu Ala Glu Pro Met Glu Gln Asn Pro Pro Gln Gln Gln Arg
        210                 215                 220
Leu Ala Leu His Asn Pro Leu Pro Lys Ala Lys Pro Gly Thr His Leu
225                 230                 235                 240
Pro Gln Gly Pro Ser Ser Arg Thr His Pro Gly Pro Leu Ala Gly Arg
            245                 250                 255
His Phe Asn Leu Ala Pro Leu Gly Arg Arg Val Gln Ser Gln Trp
        260                 265                 270
Ala Ser Thr Arg Gly Gly His Lys Glu Arg Pro Thr Val Met Leu Phe
        275                 280                 285
Pro Phe Arg Asn Leu Gly Ser Pro Thr Gln Val Ile Ser Asn Pro Glu
        290                 295                 300
Ser Lys Glu Glu His Ala Ile Tyr Thr Ala Asp Leu Ala Met Gly Thr
305                 310                 315                 320
Arg Ala Pro Ser Asn Gly Lys Tyr Lys Gly Pro Tyr Gln Thr Leu Gly
            325                 330                 335
Gly Arg Ala Leu Lys Glu Asn Pro Val Asp Leu Pro Ala Thr Glu Gln
            340                 345                 350
Lys Glu
```

<210> SEQ ID NO 3
<211> LENGTH: 1704
<212> TYPE: DNA
<213> ORGANISM: mouse
<220> FEATURE:
<221> NAME/KEY: misc_feature
<222> LOCATION: (1687)..(1687)
<223> OTHER INFORMATION: "n" represents "A" because it is in the poly A tail of the cDNA

<400> SEQUENCE: 3

```
gcattttaag tttagtgatc tggacaggtt gatacactta agtcaccgcc tgagaggaga      60
ctgcggggtt cccgtggctc cgcgaaatgg gcccagctgg tccgccgacc ttccggtgca     120
gatgagagaa gcgggctccg cctacgggag cgtccggga agcctgggtt gaacgaaagg      180
aggaaagggc gcccgcgggc catggcccca cctccagggg taggtcccgc gtctctgcgg     240
tttgctgccg ccgccagctg gctggtagtc cgccgtcgcc gcgtagagca cttcccgaaa     300
gtggtggagt ttctgcagtc cttgcgcgct gctgccccg gcttggtttg ctaccggcac      360
catgaacgcc tgtgtatgag cctaaaggcc aaggtggtgg tggagctgat cctgcaggcg    420
cgaccctggg accaggtcct gaatgccctg aagcatcact tccagcagag gtccagaaca     480
acaaagaag acaggaagct tttggaggca cgggaaaatt tttgcttgct tgtgaagcac      540
```

-continued

```
ctgtcagagg acccgccttc gagcctgcag gaactagaac aagactatgg ggaatccttt      600
ctagttgcca tggaaaagct gttgtttgaa tacttgtgtc agctagagaa agcactgcct      660
ccagtcagag cacaagagct tcaggatgct ctaagttgga gtcagccggg ctcgttcatc      720
acttcttcgg ttgctttgca ccagtatggt atggacatgg ggtggacatt tccagagagc      780
tctacttctg gctcagggaa tctgatagag cccatggaag agggtcctca tcagcaaacc      840
aggccagcat tccacagtcc tctgcctaaa gctaagcttg gccctcacca gccagcttca      900
ctggagcacc cagaacactt agctggccac cgctttaatc tggccccttt gggaaagcga      960
aaatcccgat cacattggac atcggcaaag gcgtgccata agagcggcc cacagtcatg      1020
ctactcccat ttaggaacat gggcttacca gctcaagact tatctaaccc taaaagcagg      1080
gaagaacccg gtgcggcctc agcagcttct gtgggaacag agccagtctg cacggaggag      1140
gctaagactc catctcggcc tttggggaaa agggcattag aggagacccc acctgactca      1200
ccggctgcag agcaggagaa cagtgtgaat tgcgtggatc ctctaagaca ctcatcaccg      1260
cctctttcag tcaagaaacc agtgctgtcc ccaaccccgt gtagctctgt tattaccata      1320
ggggacttgg ttttggactc tgatgaggaa gaaaataacc agaaggaagg gaaggagttt      1380
ttgaaaaact accagaagac gaagtttgac acctatatcc ccatgttttg tgactacatc      1440
ccgtagtgtc ctgcctattc ctttctggct acctaaacgg ttctcactca ggtcctctgg      1500
aatattctct gcactctgtc catcttctgc tgcagctctg catgcaattt agtggaaaag      1560
aagaggaagt ccagacttga gttgcctggc tacattgctg aaagctttgt agcacttgaa      1620
aattaaatat tgatttgttt cactattgat gggaagaagg ggaataaaga cttgcatacc      1680
aaaaaanaaa aaaaaaaaa aaaa                                              1704
```

<210> SEQ ID NO 4
<211> LENGTH: 414
<212> TYPE: PRT
<213> ORGANISM: mouse

<400> SEQUENCE: 4

```
Met Ala Pro Pro Gly Val Gly Pro Ala Ser Leu Arg Phe Ala Ala
1               5                   10                  15

Ala Ala Ser Trp Leu Val Val Arg Arg Arg Val Glu His Phe Pro
            20                  25                  30

Lys Val Val Glu Phe Leu Gln Ser Leu Arg Ala Ala Pro Gly Leu
        35                  40                  45

Val Cys Tyr Arg His His Glu Arg Leu Cys Met Ser Leu Lys Ala Lys
    50                  55                  60

Val Val Glu Leu Ile Leu Gln Ala Arg Pro Trp Asp Gln Val Leu
65                  70                  75                  80

Asn Ala Leu Lys His His Phe Pro Ala Glu Ser Arg Thr Thr Lys Glu
                85                  90                  95

Asp Arg Lys Leu Leu Glu Ala Arg Glu Asn Phe Cys Leu Leu Val Lys
                100                 105                 110

His Leu Ser Glu Asp Pro Pro Ser Ser Leu Gln Glu Leu Glu Gln Asp
                115                 120                 125

Tyr Gly Glu Ser Phe Leu Val Ala Met Glu Lys Leu Leu Phe Glu Tyr
            130                 135                 140

Leu Cys Gln Leu Glu Lys Ala Leu Pro Pro Val Arg Ala Gln Glu Leu
145                 150                 155                 160
```

-continued

```
Gln Asp Ala Leu Ser Trp Ser Gln Pro Gly Ser Phe Ile Thr Ser Ser
                165                 170                 175

Val Ala Leu His Gln Tyr Gly Met Asp Met Gly Trp Thr Phe Pro Glu
                180             185                 190

Ser Ser Thr Ser Gly Ser Gly Asn Leu Ile Glu Pro Met Glu Glu Gly
        195             200                 205

Pro His Gln Gln Thr Arg Pro Ala Phe His Ser Pro Leu Pro Lys Ala
        210             215                 220

Lys Leu Gly Pro His Gln Pro Ala Ser Leu Glu His Pro Glu His Leu
225             230                 235                 240

Ala Gly His Arg Phe Asn Leu Ala Pro Leu Gly Lys Arg Lys Ser Arg
                245                 250                 255

Ser His Trp Thr Ser Ala Lys Ala Cys His Lys Glu Arg Pro Thr Val
                260                 265                 270

Met Leu Leu Pro Phe Arg Asn Met Gly Leu Pro Ala Gln Asp Leu Ser
                275                 280                 285

Asn Pro Lys Ser Arg Glu Glu Pro Gly Ala Ala Ser Ala Ala Ser Val
        290                 295                 300

Gly Thr Glu Pro Val Cys Thr Glu Glu Ala Lys Thr Pro Ser Arg Pro
305                 310                 315                 320

Leu Gly Lys Arg Ala Leu Glu Glu Thr Pro Pro Asp Ser Pro Ala Ala
                325                 330                 335

Glu Gln Glu Asn Ser Val Asn Cys Val Asp Pro Leu Arg His Ser Ser
                340                 345                 350

Pro Pro Leu Ser Val Lys Lys Pro Val Leu Ser Pro Thr Pro Cys Ser
            355                 360                 365

Ser Val Ile Thr Ile Gly Asp Leu Val Leu Asp Ser Asp Glu Glu Glu
        370                 375                 380

Asn Asn Gln Lys Glu Gly Lys Glu Phe Leu Lys Asn Tyr Gln Lys Thr
385                 390                 395                 400

Lys Phe Asp Thr Tyr Ile Pro Met Phe Cys Asp Tyr Ile Pro
                    405                 410
```

POLYNUCLEOTIDES ENCODING TRF1 BINDING PROTEINS

RELATED APPLICATIONS

This application claims priority of Provisional Application Ser. No. 60/142191 filed Jul. 1, 1999.

GOVERNMENT RIGHTS

The United States Government has rights in this invention pursuant to Contract No. DE-AC03-76SF00098 between the United States Department of Energy and the University of California.

This invention was supported by research and training grants from the National Institute on Aging and with U.S. government support under Contract No. DE-AC03-76SF00098 between the U.S. Department of Energy and the University of California for the operation of Lawrence Berkeley National Laboratory (LBNL). The U.S. government may have certain rights in the invention.

FIELD OF THE INVENTION

The invention relates to a novel gene encoding a protein that associates with human telomeres, and to compounds that interact with telomeric DNA binding proteins, thereby acting to extend or shorten telomere length.

BACKGROUND OF THE INVENTION

Telomeres are DNA-protein structures that cap the ends of linear eukaryotic chromosomes. Telomeres consist of several thousand copies of a repetitive DNA sequence (TTAGGG in vertebrates), and an unknown number of proteins. The telomeric nucleic acid-protein structure is essential for preventing chromosome end-to-end fusions and, thus, for maintaining genomic stability (Zakian, 1989; Blackburn, 1991). Telomeres can also influence gene expression. In lower eukaryotes, genes located near telomeres are silenced, and proteins that mediate this silencing can alter gene expression at non-telomeric loci (Aparicio et al., 1991; Brachmann et al., 1995; Marchand et al., 1996). In higher eukaryotes, telomere shortening causes striking changes in cell phenotype (Campisi, 1997). The ability of telomeres to prevent genomic instability and alter gene expression depends on their length and the proteins that associate with them.

The human germ line and early embryonic cells maintain an average telomere or terminal restriction fragment (TRF) length of 15–20 kb. This length is maintained in part by telomerase, a ribonucleoprotein reverse transcriptase (Greider, 1996; Lingner & Cech, 1998; Nugent & Lundblad, 1998). Most human cells do not express telomerase. Because DNA replication is bidirectional, initiated from a labile primer and catalyzed by a unidirectional polymerase, each cell cycle leaves unduplicated 50–200 bp at the 3' terminus (Levy et al., 1992). Telomerase uses this 3' overhang to add back single-stranded telomeric repeats, but proliferating cells that lack telomerase lose telomeric DNA. After 50–80 divisions, most human cells have TRFs of only 4–7 kb, at which point they enter an irreversible state of arrested growth and altered function termed replicative senescence (Harley et al., 1990; Shay & Wright, 1991; Dimri et al., 1995; Campisi et al., 1996). Replicative senescence is an important tumor suppressive mechanism, and the accumulation of dysfunctional senescent cells may contribute to certain age-related pathologies (Sager, 1991; Harley & Villeponteau, 1995; Campisi, 1996, 1997; Yeager et al., 1998).

Ectopic expression of telomerase prevents telomere erosion and senescence in some, but not all, human cells (Bodnar et al., 1998; Vaziri & Benchimol, 1998; Kiyono et al., 1998). In addition, viral oncoproteins that inactivate the cellular tumor suppressors p53 and pRb delay or prevent senescence (Weinberg, 1991). Such proteins do not, however, prevent telomere shortening. Human cells lacking p53 and pRb function can proliferate until the telomeres become very short (<2 kb) and the genome unstable, whereupon cells with an indefinite or immortal replicative life span may emerge (Shay & Wright, 1991). Immortalization renders cells highly susceptible to tumorigenic transformation (Sager, 1991), but tumor cells cannot survive unless they acquire a means to maintain their telomeres. The most common means is induction of telomerase (Kim et al., 1994), but recombination can also prevent telomere loss (Bryan et al., 1997). In addition to telomerase, telomere length is regulated by exonuclease activity, and telomere-associated proteins that may determine whether and how telomerase gains access to the 3' terminus (Greider, 1996; Shore, 1997; Lingner & Cech, 1998).

Lower eukaryotes such as *Saccharomyces cerevisiae* maintain telomeres by a balance between elongation by telomerase and shortening by exonuclease activity. This equilibrium is controlled in part by Rap1, a double-stranded telomeric DNA binding protein. Rap1 negatively regulates telomere length, and maintains chromosome stability and telomeric silencing (Conrad et al., 1990; Kyrion et al., 1992). At least two Rap1 binding proteins, Rif1p and Rif2p, are important for Rap1p function (Hardy et al., 1992; Wotton & Shore, 1997). In addition, Rap1 associates with components of the Sir complex, which regulate silencing at telomeric and non-telomeric loci (Cockell et al., 1995; Marchand et al., 1996). Yeast proteins that associate with the telomeric 3' overhang have also been identified, two of which, Cdc13 and its binding protein Stn1, negatively regulate telomere length (Grandin et al., 1997; Nugent et al., 1996).

Three genes encoding human telomere-associated proteins have been cloned. Trf1 (Chong et al., 1995), the first such gene, may be a functional homologue of Rap1. Trf1 and its alternately spliced form Pin2 (Shen et al., 1997) bind double-stranded telomeric DNA and negatively regulate telomere length (van Steensel & de Lange, 1997). Trf1 also promotes parallel pairing of telomeric DNA tracts (Griffith et al., 1998). Trf2 is architecturally similar to Trf1, prevents chromosome fusions (van Steensel et al., 1998). A third protein, tankyrase, was recently identified as a Trf1-interacting protein and shown to have poly-ADP ribosylase activity (Smith et al., 1998).

The identification of proteins that modulate telomere length and telomerase activity provides important tools for the diagnosis and treatment of human disease. Compounds that inhibit telomerase activity can be used to treat cancer, as cancer cells express telomerase activity and normal human somatic cells do not express telomerase activity at biologically relevant levels (i.e., at levels sufficient to maintain telomere length over many cell divisions). There is a need for compounds that act as telomerase inhibitors and for compositions and methods for treating cancer and other diseases in which telomerase activity is present abnormally. Certain age-related disorders may be treated by lengthening telomeres (e.g., improvements in wound healing, immune response).

Accordingly, it is an object of the present invention to provide a novel recombinant protein (termed herein "Tin2") that is associated with other telomere binding proteins.

It is further an object of the present invention to provide a polynucleotide useful in the production of this protein.

It is another object of the invention to provide materials and methods useful in the evaluation of the ability of test substances to modulate telomere length.

It is also an object of the present invention to provide materials and methods which can be useful in evaluating the telomere status of a subject cell.

It is another object of the invention to provide antibodies to Tin2, said antibodies being useful in measuring the expression of Tin2.

It is an additional object of the present invention to provide nucleic acids in the form of Tin2 probes for detecting the presence of the,Tin2 gene and/or Tin2 transcription.

It is also an object of the present invention to provide a composition and method for the promotion clustering of telomeric DNA tracts.

SUMMARY OF THE INVENTION

The present invention comprises a protein, Tin2, that associates with mammalian telomeres. Tin2 interacts with Trf1, and negatively regulates telomere length. Tin2 does not directly bind DNA, but mediates formation of a Tin2-Trf1-telomeric DNA multiplex that limits telomerase access to the telomere. Tin2 also aligns telomeric DNA tracts.

The present invention provides polynucleotide (specifically cDNA) sequences that encode a novel Trf1 binding protein having approximately 354 amino acids. The encoded wild-type Tin2 protein negatively regulates telomere length. In addition, mutant DNA and proteins are provided that contain deletions in the wild-type structures. These mutant proteins can induce elongation of telomeres in telomerase-positive cells.

Using the DNA sequences for human Tin2 provided herein, one can also obtain nucleic acid probes specific for the Tin2 gene or the Tin2 mRNA. These probes can be used to ascertain the status of a test cell as to (a) whether it possesses the Tin2 gene or (2) whether and how much it is expressing Tin2.

Using the DNA sequences for human Tin2 provided herein, one can also obtain related genes from other species or Tin2 homologs, such as the mouse.

Furthermore, antibodies are provided herein which are specific to Tin2. Polyclonal antibodies have been produced in rabbits, and monoclonal antibodies can be produced by known methods. These antibodies can be used to ascertain the Tin2 localization in a test cell, as well as the expression of Tin2 in a test cell.

Also provided are assay methodologies that utilize the Tin2 protein, DNA or antibody herein provided to screen potential therapeutic compounds that inhibit or increase (mimic) Tin2 or telomerase function. It is believed that since the Trf1-Tin2 complex inhibits telomerase function, a test compound that inhibits the binding of Tin2 to Trf will increase telomerase activity. A compound that mimics wild type Tin2 by preventing association between telomerase and the Trf1 complex would inhibit telomerase activity.

Finally, the present Tin2 DNA and protein could be added to cells to provide either decreased telomerase activity (wild type) or increased telomerase activity (mutated). A specific mutation, truncation Tin2–13 is especially preferred to increase wild-type telomerase activity, i.e., telomere length. The Tin2 constructs of the present invention may be delivered to host cells by transfection with retroviral vectors package using a known packaging cell line. The coat protein is trophic for human and animal cells.

BRIEF DESCRIPTION OF THE DRAWINGS

FIG. 1 is a diagrammatic representation of the Tin2 protein of the present invention with other molecules thought to interact with Tin2 and its associated molecules;

DESCRIPTION OF THE PREFERRED EMBODIMENT

Figure 2:
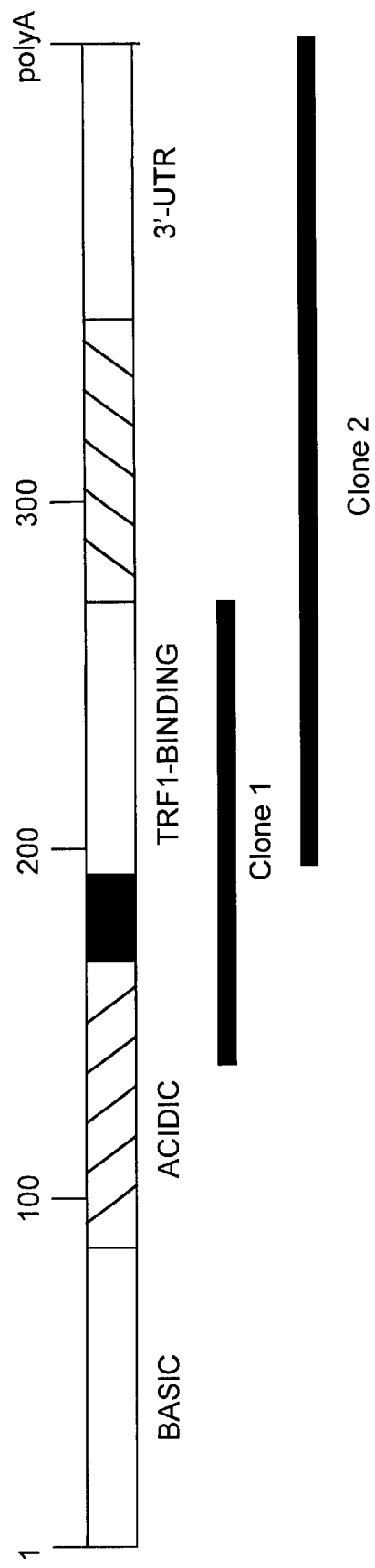
FIG. 2 shows the structural features of Tin2 as deduced from the amino acid sequence and Trf binding experiments; also shown are Clone 1 and Clone 2 obtained in the original cloning of Tin2.

To facilitate understanding and practice of the present invention in its diverse applications, the description is organized as shown in the examples below; which are given to illustrate but not limit the invention. Generally, the nomenclature used herein and many of the laboratory procedures in cell culture, molecular genetics and nucleic acid chemistry and hybridization described below are those well known and commonly employed in the art.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, preferred methods and materials are described. For purposes of the present invention, the following terms are defined below.

"Antibody" refers to naturally occurring and recombinant polypeptides and proteins encoded by immunoglobulin genes, or fragments thereof, that specifically bind to or "recognize" an analyte or "antigen". Immunoglobulin genes include the kappa, lambda, alpha, gamma, delta, epsilon and mu constant region genes, as well as myriad immunoglobulin variable region genes. An antibody can exist as an intact immunoglobulin or as any one of a number of well characterized fragments, e.g., Fab' and F(ab)'2 fragments, produced by various means, including recombinant methodology and digestion with various peptidases. "cDNA" refers to deoxyribonucleic acids produced by reverse-transcription and typically second-strand synthesis of mRNA or other RNA produced by a gene; if double-stranded, a cDNA molecule has both a coding or sense and a non-coding or antisense strand.

"Isolated" refers to a polynucleotide that has been separated from its native environment, e.g., by nucleotide synthesis or cloning. In the case of a polypeptide, the polypeptide is separated from its native environment, by synthesis or by expression in a recombinant host cell. An isolated polynucleotide may be contained in a vector, host cell, and/or a transgenic animal.

"Label" or "labeled" refers to a detectable marker and to the incorporation of such a marker into a nucleic acid, protein, or other molecule. The label may be detectable directly, i.e., the label can be a radioisotope (e.g., $^3$H, $^{14}$C., $^{35}$S, $^{125}$I, $^{131}$I) or a fluorescent or phosphorescent molecule (e.g., FITC, rhodamine, lanthanide phosphors), or indirectly, i.e., by enzymatic activity (e.g., beta-galactosidase, luciferase, alkaline phosphatase) or ability to bind to another molecule (e.g., streptavidin, biotin, an epitope). Incorporation of a label can be achieved by a variety of means, i.e., by use of radiolabeled or biotinylated nucleotides in polymerase-mediated primer extension reactions, epitope-tagging, or binding to an antibody. Labels can be attached directly or via spacer arms of various lengths to reduce steric hindrance.

"Pairing" and "clustering" refer to two related phenomenon where telomeric regions of DNA, in DNA probes or in chromosomes, associate or adhere to each other, where the adhesion is mediated by proteins. Pairing, for example, can refer to the association of two DNA probes with each other, as mediated by Trf-1 and Tin-2. Pairing can occur within one telomeric tract, and it can occur between two different telomeres. Clustering, which can be observed in vivo, may involve multiple chromosomes, and most probably Trf-1, Tin-2, and other proteins.

"Polynucleotide" or "nucleic acid" refers to an oligonucleotide and is typically used to refer to oligonucleotides greater than 30 nucleotides in length. Conventional notation is used herein to portray polynucleotide sequences: the left-hand end of single-stranded polynucleotide sequences is the 5'-end; the left-hand direction of double-stranded polynucleotide sequences is referred to as the 5'-direction. The direction of 5' to 3' addition of nucleotides to nascent RNA transcripts is referred to as the transcription direction; the DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences". Polynucleotides and recombinantly produced protein, and fragments or analogs thereof, may be prepared according to methods known in the art and described in Maniatis et al., Molecular Cloning: A Laboratory Manual, 2nd Ed., (1989), Cold Spring Harbor, N.Y., and Berger and Kimmel, Methods in Enzymology, Volume 152, Guide to Molecular Cloning Techniques (1987), Academic Press, Inc., San Diego, Calif., which are incorporated herein by reference.

"Polypeptide," "peptide" and "protein" are used interchangeably herein to refer to a polymer of amino acid residues and to variants and synthetic analogs of the same. Thus, these terms apply to amino acid polymers in which one or more amino acid residues is a synthetic non-naturally occurring amino acid, such as a chemical analog of a corresponding naturally occurring amino acid, as well as to naturally occurring amino acid polymers. Conventional notation is used herein to portray polypeptide sequences: the left-hand end of polypeptide sequences is the amino-terminus; the right-hand end of polypeptide sequences is the carboxy-terminus. The term "recombinant protein" refers to a protein that is produced by expression of a recombinant DNA molecule that encodes the amino acid sequence of the protein. Terms used to describe sequence relationships between two or more polynucleotides or polypeptides include "reference sequence", "comparison window", "sequence identity", "percentage of sequence identity", and "substantial identity". A "reference sequence" is a defined sequence used as a basis for a sequence comparison and may be a subset of a larger sequence, i.e., a complete cDNA, protein, or gene sequence. Generally, a reference sequence is at least 12 but frequently 15 to 18 and often at least 25 nucleotides (or other monomer unit) in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically at least 12 contiguous residues that is compared to a reference sequence; the comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

"Probe" refers to a molecule that binds to a specific sequence or subsequence or other moiety of another molecule. Unless otherwise indicated, the term "probe" typically refers to an oligonucleotide probe that binds to another nucleic acid, often called the "target nucleic acid", through complementary base pairing. Probes may bind target nucleic acids lacking complete sequence complementarity with the probe, depending upon the stringency of the hybridization conditions. Probes can be directly or indirectly labeled.

"Recombinant" refers to methods and reagents in which nucleic acids synthesized or otherwise manipulated in vitro are used to produce gene products encoded by those nucleic acids in cells or other biological systems. For example, an amplified or assembled product polynucleotide may be inserted into a suitable DNA vector, such as a bacterial plasmid, and the plasmid can be used to transform a suitable host cell. The gene is then expressed in the host cell to produce the recombinant protein. The transformed host cell may be prokaryotic or eukaryotic, including bacterial, mammalian, yeast, Aspergillus, and insect cells. A recombinant polynucleotide may serve a non-coding function (e.g., promoter, origin of replication, ribosome-binding site, etc.) as well.

"Sequence identity" refers to sequences that are identical (i.e., on a nucleotide-by-nucleotide or amino acid-by-amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

"Specific hybridization" refers to the formation of hybrids between a probe polynucleotide (e.g., a polynucleotide of the invention which may include substitutions, deletions, and/or additions) and a specific target polynucleotide (e.g., a polynucleotide having the sequence of a TPC2 or TPC3 gene or gene product), wherein the probe preferentially hybridizes to the specific target and not to other polynucleotides in the mixture that do not share sequence identity with the target.

"Stringent conditions" refer to temperature and ionic conditions used in nucleic acid hybridization. The stringency required is nucleotide sequence dependent and also depends upon the various components present during hybridization. Generally, stringent conditions are selected to be about 5 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

"Telomere length regulatory protein" and "telomerase regulatory protein" refers to polypeptides involved in telomere metabolism and telomerase activity. Such proteins include telomerase, the protein components of telomerase, proteins that selectively bind nucleic acids containing telomere repeat sequences or telomeric ends, proteins required for telomere repair, maintenance, and/or elongation, and proteins necessary for expression or formation of active telomerase enzyme. Although the present invention relates to such proteins generally, mammalian telomerase, and particularly human telomerase, and related proteins are provided as preferred embodiments.

"Telomerase activity" refers to the ability of telomerase protein components to associate with one another and the RNA component of telomerase either in vivo or in vitro into a multi-component enzyme that can elongate telomeric DNA. A preferred assay method for detecting telomerase activity is the TRAP assay. See PCT patent publication No. 95/13381, supra. This assay measures the amount of radioactive nucleotides incorporated into elongation products, polynucleotides, formed by nucleotide addition to a telomerase substrate or primer. The radioactivity incorporated can be measured as a function of the intensity of a band on a Phosphorlmager.™. screen exposed to a gel on which the radioactive products are separated. A test experiment and a control experiment can be compared by visually using the Phosphorlmager.™. screens. See also the commercially available TRAP-eze.™. telomerase assay kit (Oncor); and Morin, 1989, Cell 59: 521–529.

"Tin2" refers to a telomere-associated protein which binds Trf1 and regulates telomere length. The protein promotes the pairing or clustering of telomere DNA tracts. It comprises a basic domain, an acidic domain, and a Trf-1 binding domain. The specific amino acids and pI of the human Tin2 two highly basic domains and the following acidic domain are set forth in Example 1. Fragments of Tin2 which have biological activity are also disclosed herein. These have the core Tin2 sequence but certain portions of the sequence have been omitted. For example, the human Tin2 contains 354 amino acids. Tin2 lacks amino acids 1–120; Tin2–13 lacks amino acids 1–196; Tin2–14 lacks amino acids 276–354; and Tin2–15 lacks amino acids 197–354. As discussed in Example 6, Tin2 proteins bind to the TRF1-DNA complex. A "TRF protein" means a protein that binds to the terminal restriction fragment component of telomeres. The most notable example is TRF-1, which negatively regulates telomere length, as does Tin2.

"Tin2 homolog" refers to a protein having a Tin2 actvity and at least 30% sequence homology to Tin-2 at the amino acid level. Homology is calculated with a standard alignment tool, such as BLAST or FASTA with default parameters.

"Yeast two-hybrid"system" refers to a system that utilizes expression vectors that encode the predetermined polypeptide sequence as a fusion protein and is used to identify protein-protein interactions in vivo through reconstitution of a transcriptional activator (see Fields and Song, 1989, Nature 340:245). Usually the yeast Gal4 transcription protein, which consists of separable domains responsible for DNA-binding and transcriptional activation, serves as the transcriptional activator. Polynucleotides encoding two hybrid proteins, one consisting of the yeast Gal4 DNA-binding domain fused to a polypeptide sequence of a first protein and the other consisting of the Gal4 activation domain fused to a polypeptide sequence of a second protein (either the first or second protein typically is a number of different proteins to be screened for ability to interact specifically with the other protein), are constructed and introduced into a yeast host cell. Intermolecular binding, if any, between the two fusion proteins reconstitutes the Gal4 DNA-binding domain with the Gal4 activation domain, which leads to the transcriptional activation of a reporter gene (e.g., lacZ, HIS3) operably linked to the Gal4 binding site. Typically, the two-hybrid method is used to identify novel polypeptide sequences which interact with a known protein.

Discussion

Trf1, the first human telomeric protein to be cloned, binds double-stranded telomeric DNA (Chong et al., 1995) and promotes parallel pairing of telomeric DNA tracts (Griffith et al., 1998). Truncated forms of Trf1 increase telomere length (van Steensel & de Lange, 1998), suggesting that wild-type Trf1 negatively regulates telomere length. Tin2 is a newly isolated human telomere-associated protein that binds Trf1 in vitro and in cells, and co-localizes with Trf1 at the telomeres. Tin2 shares a number of properties with Trf1. Like Trf1, Tin2 was widely and essentially constitutively expressed. It may also be conserved among vertebrates because there are murine expressed sequence tags that show >90% identity to human Tin2. Truncated forms of Tin2, (described below), elongated the telomeres, demonstrating that wild-type Tin2 is also a negative regulator of telomere length. In addition, Tin2 markedly stimulated the ability of telomeric DNA tracts to interact. However, Tin2 did not bind telomeric DNA directly. Thus, these activities of Tin2 depended on its ability to bind Trf1. Tin2 is an important component of the telomeric structure and regulates many of the properties of Trf1.

Tin2 may be functionally homologous to Rif proteins, which, together with Rap1, control telomere length. Rap1 and its associated proteins (Sir proteins) also function in gene silencing at telomeric and non-telomeric sites. It is believed that Tin2 is functionally homologous to SIR proteins and functions in gene silencing at telomeric and non-telomeric sites.

While the inventors do not wish to be bound by any theory of operation of Tin2, two results described below suggest that Tin2 regulates telomere length by promoting a structure that limits the ability of telomerase to access the telomere. This structure is illustrated schematically in FIG. 1. First, a dominant negative mutant extended telomere length only in telomerase-positive cells. There was no effect on telomere length in normal cells, but normal cells transfected with a telomerase cDNA showed telomere elongation indicating that telomere length control by Tin2 was telomerase-dependent. However, there was no evidence for a direct effect of Tin2 on telomerase activity because the addition of recombinant Tin2 to an in-vitro telomerase assay (TRAP assay) did not inhibit activity. In addition to demonstrating an indirect mode of regulation, these data indicate that, at least in normal cells, Tin2 does not negatively regulate telomere length by suppressing the recombinational pathway that can extend telomeres in some tumor cells (Bryan et al., 1997). Second, Tin2 mutants (FIG. 4) that retained Trf1-binding but lacked the N-terminus (120 or 196 aa) extended telomere length. This finding raised two possibilities: the N-terminus binds telomerase inhibitors that cannot associate with the telomere when N-terminally deleted Tin2 proteins are bound, or the N-terminus promotes a compact telomeric structure and its absence opens the structure, thereby giving telomerase greater access. Our electophoretic mobility shift assay ("EMSA") analyses with purified proteins, and the finding that Tin2 markedly stimulated the interaction of telomeric DNA tracts with each other, support the latter possibility. Since the Tin2 mutant that induced the greatest telomere elongation in vivo (Tin2–13, (FIG. 4)) was strikingly deficient in stimulating telomeric DNA interactions, pairing or higher order clustering of telomeric DNA is important for telomere length regulation by telomerase. Tin2 may stimulate the parallel pairing activity of Trf1 (Griffith et al., 1998), and/or it may promote anti-Parallel pairing of telomeric DNA, which would favor an even more compact structure.

As stated, we believe that Tin2 stimulates the aggregation of telomeric DNA segments within the telomere, creating a folded or coiled structure that renders the 3' overhang relatively inaccessible to telomerase. The Trf1-binding domain (aa 196 to 276) and the N-terminal 196 aa are important for this activity. Tin2–13, because it binds Trf1 but lacks the N-terminal 196 aa, may cause an open telomeric structure in which the 3' terminus is more accessible to telomerase. Although Tin2–13 was expressed at very low levels in cells, it showed potent dominant negative activity, (i.e., it occurred even in the presence of wild type Tin2, extending the average TRF to 15 kb.) Tin2–12 extended the telomeres to only 6–7 kb, despite higher levels of expression. Because Tin2–12 binds Trf1 but lacks only 120 N-terminal aa, a relatively large region within the Tin2 N-terminus (>76 aa) may be critical for compacting the telomeric structure. Tin2 stimulates interaction among telomeric DNA tracts by binding two Trf1 molecules, thereby forming a bridge between Trf1-bound DNA tracts or may induce a conformational change in Trf1, and increase its ability to promote parallel pairing or allow it to also promote anti-parallel pairing.

Our data suggests that Tin2 and Trf1 are sufficient to induce telomeric DNA tract interactions. However, other nuclear proteins help stabilize the structure. Consistent with this view, nuclear extract proteins increased the Tin2/Trf1/telomeric DNA complexes formed in vitro. Moreover, the Tin2–15 mutant, which does not bind Trf1 and contains only the N-terminal 196 aa, also extended telomere length (to 10–12 kb) despite low levels of expression. This demonstrates that the N-terminus interacts with telomere-associated proteins other than Trf1 that help maintain the telomeric structure and regulate telomere length in vivo. Some cancer cells (10–20%) are immortal but lack telomerase. These cancer cells are believed to survive by replenishing their telomeres through recombination. Such cells are said to be hyper-recombinational or hyper-rec. This pathway of maintaining telomeres without telomerase is called the ALT pathway. Tin2 colocalizes in large foci with BLM, a helicase believed to be important for recombination in ALT cells. Colocalization of BLM and Tin2 was not seen in non-ALT cells. This finding demonstrates that Tin2 may participate in recombination.

Tin2 facilitates interchromosomal telomere pairing during meiosis, where proper alignment of chromosomes is critical. In this regard, it is interesting that Taz1, the Trf1 homologue in the yeast S. pombe, is essential for meiosis (Cooper et al., 1998). By analogy with the model by which RecA facilitates homologous recombination (Griffith et al., 1998), in which protein-protein interactions rather than protein-DNA or DNA-DNA interactions are crucial, the Tin2-Trf1 interaction is important for DNA recombination events.

General Materials and Methods

Cell Culture.

WI-38 cells were grown and made quiescent or senescent, as described (Dimri et al., 1994; Dimri et al., 1995). Human tumor cells HT1080, U0OS, HTB9 and C33A were from the American Type Culture Collection. MDA-452 cells were from R. Lupu, and HMT-3522 cells were from M. Bissell (Berkeley National Lab). Tumor cells were grown in medium used for WI-38 cells, and HMT-3522 cells were grown in a chemically defined medium (Briand et al., 1987).

Northern and Western Analyses.

Northern analysis was performed as described (Dimri et al., 1994). Membranes with 2 ng poly-A+ RNA from human tissues (Clontech), or 30 ng total RNA from cultured cells, were hybridized with a Tin2 probe (Clone 2) and rehybridized with B-actin or QM (Dimri et al., 1996) control probes. Western analysis was performed as described (Dimri et al., 1996), using enhanced chemiluminescence (Amersham) and autoradiography for detection.

Retroviruses.

Figure 4:
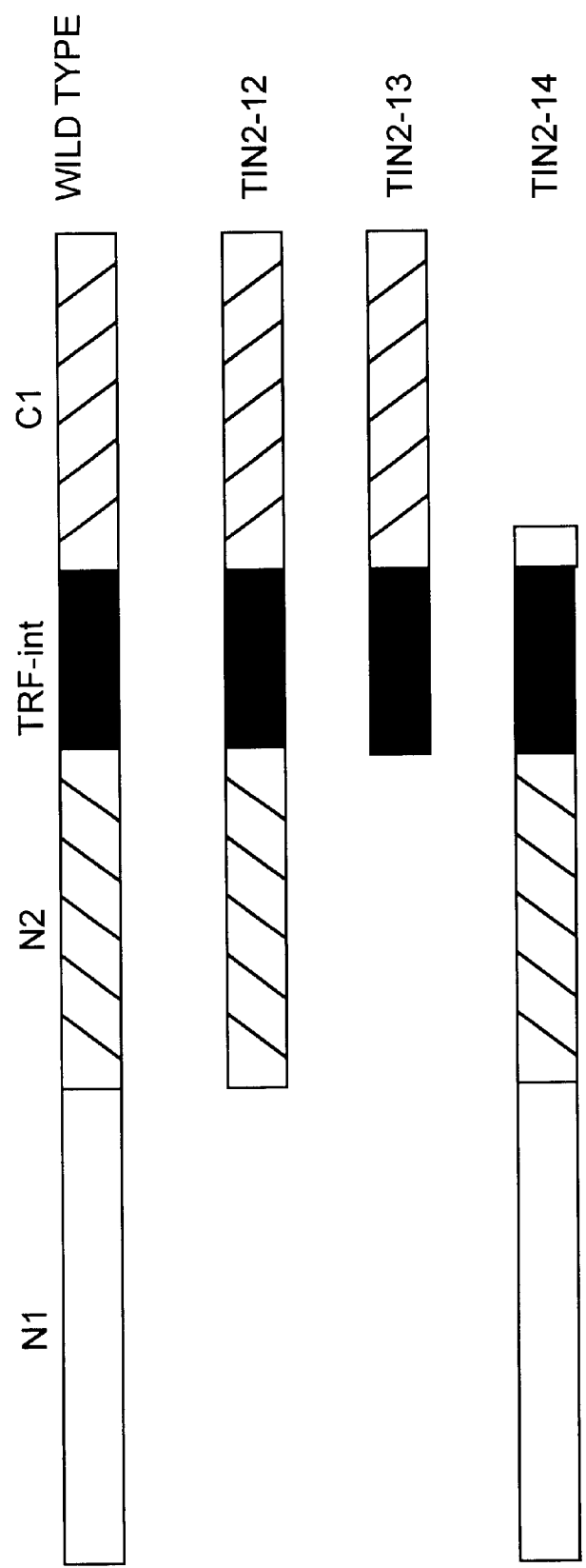
FIG. 4 shows various Tin2 truncated mutants in comparison with the wild-type and its various N1, N2, Trf-int and C1 domains, as described below.

Amphotrophic retroviruses were produced and used to transfect human cell lines. The effect of the transfected Tin2 constructs on the transfected human cell lines is shown in FIG. 4. Various commercial and pre-existing components were used to create infectious, replication deficient viral particles. Tin2 was cloned into a retroviral vector plasmid pLXSN, with a Psi packaging signal, from Clontech, Inc., Genbank Accession No. M28248, Finer et al. 1994. Tsa54 cell line (a 293 cell line derivative) was infected with a vector containing packaging genes gag, pop, env, termed "PIK" and obtained from Cell Genesys. The Tsa54 cells were also infected with pLXSN-Tin2, resulting in viral particles containing the constructs for Tin2, Tin2–13, etc. Another packaging cell line that may be used is the Amphopack-293 cell line from Clontech, which has integrated into its genome the gag, pol and env genes, e.g., from HTLV. PLXSN is described in Miller, A. D. and Rossman, G. J. Biotechniques 7: 980–988 (1989)). pBABE-puro, (Morganstern, J. P. and Land, H. Nucleic Acids Research, 18: 3587–3596 (1990)) may also be used. These vectors are cotransfected with a plasmid encoding viral coat and other proteins (from Cell Genesys) into a cell line Tsa54 (from Cell Genesys) that amplifies the plasmids using the Sv40T antigen and assembles the virus.

The virus sheds from cell membranes into the culture medium. Culture medium containing virus was frozen, thawed, and assayed for reverse transcriptase (RT). Proliferating cells were infected with equivalent RT units. pLXSN-infected cells were selected for 5 d in 400 ng/ml G-418 and grown in 100 ng/ml G418. pBabe-infected cells were selected for 7 d in 0.75 ng/ml puromycin and grown without the drug.

Polyclonal Antibody Production and Immunolocalization.

Tin2 aa 121–354 fused to GST (GST-Tin2$_{121-354}$) was used to produce polyclonal antibodies in rabbits using a standard protocol by a commercial service (Babco). Antibodies were affinity purified by blotting GST-Tin2$_{121-354}$ onto a membrane, incubating the membrane with serum plus GST, and recovering the antibodies as described by Sambrook et al. (1989). Antibodies were tested on western blots of GST and GST-Tin2, or control and Myc-Tin2-expressing cell lysates. Immunostaining was carried out as described by Compton et al. (1991). Cells grown on coverslips were stained with anti-HA or anti-Tin2 antibodies for 1 h at room temperature. Secondary antibodies were FITC-IgG or biotinylated IgG followed by Texas red-streptavidin (Vector Laboratories). Cells grown in colcemid (0.2 ug/ml) for 3 h were lysed in hypotonic buffer, and metaphase chromosomes were deposited onto poly-lysine-coated slides for staining. Cells and chromosomes were mounted in medium containing DAPI (Vector Laboratories).

Telomere Length and Telomerase Measurements.

DNA was isolated, digested with Hinfl and Rsal, and analyzed by Southern blotting using a $(TTAGGG)_3$ probe, as described (Harley et al., 1990). Hybridization signals were quantified using a phosphorimager and ImageQuant. Telomerase activity was determined by the telomere repeat amplification protocol (TRAP), using a commercial kit (Oncor/Intergen).

Electrophoretic Mobility Shift Assays (EMSA).

Nuclear extracts were prepared as described (Dimri et al., 1994), and dialyzed against 20 mM HEPES, pH 7.9, 100 mM KCl, 0.5 mM DTT, 0.5 mM PMSF. $[TTAGGG]_6$ and $[TTAGGG]_{13}$ in pBluescript were excised, labeled using Klenow or PCR and gel purified. EMSA was performed as described (Zhong et al., 1992) in 20 ul containing 0–20 ug GST or GST-fusion proteins, 6–8 ug nuclear extract protein or 5 ul in vitro translation reaction, using a 30 min incubation at room temperature and 5% PAGE run with 1× Tris-borate-EDTA buffer.

Analysis of Telomeric Probe Interactions.

Probes were synthesized by PCR. The 178 bp 6X-Tel probe was labeled using $^{32}$P-dCTP and PCR. The 126 bp Bi-6X-Tel probe was biotinylated at the 5' end using a biotinylated primer and PCR, and was unlabeled or labeled. Probes were incubated with proteins in scaled-up (5×) EMSA reactions (Zhong et al., 1992). 15 ul were analyzed by EMSA, and 85 ul were incubated with 20 ul streptavidin-agarose (50% slurry) and 500 ul EMSA buffer for 60 min at 4° C. Beads were collected by centrifugation, washed with EMSA buffer, and extracted with phenol. Released probes were precipitated with ethanol, solubilized, separated by PAGE using 5% gels containing 7.5 M urea, and analyzed using a phosphorimager and ImageQuant software.

Telomerase Activity Assays.

Telomerase activity was assayed by a modification of the method of Morin, 59 Cell 521, 1989. Aliquots (20 uL) of S-100 cell extract were diluted to a final volume of 40 uL containing 2 mM dATP, 2 mM dTTP, 1 mM $MgCl_2$, 1 uM $(TTAGGG)_3$ primer, 3.13 uM (50 uCi), $\alpha$-$^{32}$P-dGTP 400 Ci/mmole), 1 mM spermidine, 5 mM β-mercaptoethanol, 50 mM potassium acetate, and 50 mM Tris-acetate (pH 8.5). In some experiments reaction volumes were doubled. The reactions were incubated for 60 minutes at 30° C. and stopped by addition of 50 uL of 20 mM EDTA and 10 mM Tris-HCl (pH 7.5) containing 0.1 mg/ml RNAseA, followed by incubation for 15 minutes at 37° C. To eliminate proteins, 50 .mu.1 of 0.3 mg/ml Proteinase K in 10 mM Tris-HCl (pH 7.5), 0.5% SDS was added for 10 minutes at 37° C. Following extraction with phenol and chloroform, unincorporated $\alpha$-$^{32}$P-dGTP was separated by centrifuging the samples for 4 minutes at 500 g in a swinging bucket rotor through NICK SPIN columns (Pharmacia). DNA was precipitated by the addition of 5.3 uL of 4M NaCl, 4 ug of carrier tRNA and 500 uL of ethanol at −20° C. DNA pellets were resuspended in 3 uL of formamide loading dye, boiled for 1 minute, chilled on ice and loaded onto an 8% polyacrylamide, 7M urea sequencing gel and run at 1700 V for 2 hours using 0.6 times.TBE buffer. Dried gels were exposed to Kodak XAR-5 pre-flashed film at −70° C. with enhancing screen or to phosphoimager screens (Molecular Dynamics) for 7 days.

EXAMPLES

Example 1

Cloning of Tin2 in Yeast

The yeast two-hybrid system (Chien et al. 1991) was used to screen a human fibroblast cDNA library for genes encoding Trf1-interacting proteins.

The two-hybrid system was set up with Trf1 as bait.

Trf1 (Chong et al., 1995) was cloned from a human fibroblast cDNA library (Dimri et al., 1996) using the polymerase chain reaction (PCR), verified by sequencing, and subcloned into the yeast two-hybrid (Chien et al., 1991) vector pGBT9 (Clontech). RNA from WI-38 cells (70% senescent, 30% proliferating) was used to generate a random-/poly-dT-primed cDNA library in pGAD-10, using kits from Stratagene and Clontech. DNA from 1×10$^6$ independent transformants was transformed into yeast strains HF7C (Clontech) and PJ69-4A (James et al., 1996) with pGBT9-Trf1. Four yeast colonies grew on selective media containing 10–30 mM 3-aminotriazole, and expressed lacZ (β-galactosidase). pGAD10 plasmids rescued from these colonies yielded 0.4 kb (Clone 1) and 1 kb (Clone 2) inserts that overlapped in sequence (See FIG. 2).

Out of 2×10$^6$ yeast transformants, two had cDNA inserts (0.4 and 1.0 kb) that overlapped in sequence (FIG. 2) and identified a 2.4 kb species on northern blots of human RNA The 1 kb insert had a polyadenylation site, allowing the complete coding region to be cloned by 5' RACE. The largest RACE product contained a 1,062 bp open reading frame (ORF) flanked by a 263 bp 5' untranslated region (UTR) and 870 bp 3' UTR. The ORF encoded a 354 amino acid (aa) protein (39,752 D calculated MW), which has been named Tin2 (Trf1-interacting nuclear protein 2) (SEQ ID NO: 2).

Clone 2 was used to clone the full length cDNA using a 5' RACE kit and human fibroblast Marathon library (Clontech). RACE products were cloned into pGEM-TA (Promega), and three independent clones were sequenced. The largest product (pGEM-TA-Tin2) contained the Tin2 ORF and UTRs, and was analyzed using MacVector. Trf1 cDNA fragments were generated by PCR and cloned into pGBT9, and full length Trf1 cDNA was cloned into pGAD-10. Vectors were transformed into yeast strain Y190 (Clontech), selected and tested for LacZ expression. β-galactosidase (Bgal) was quantified in 3–5 independent transformants using a liquid luminescent assay kit (Tropix), and normalized for cell number.

The Tin2 cDNA, which directed the synthesis of a single protein that migrated with a MWd region of 40kd, is shown in SEQ ID No: 1.

Tin2 shared no significant homology with identified entries in the gene and protein sequence databases. The protein is relatively basic (pI=9.45), with a few distinguishing structural motifs (FIG. 2). The N-terminal one-third contains two highly basic domains (aa 1–45, pI=12.8; aa 45–90, pI=10.4), followed by an acidic domain (aa 90–170, pI=4.3), which have the potential to form α-helical structures. From the sequence overlap of the two-hybrid cDNA inserts, it is shown that Tin2 interacts with Trf1 via a domain between aa 196 and 276 (FIG. 2).

Example 2

Interaction between Tin2 and Trf1 in Vitro and in Yeast and Human Cells

A. Interaction in Yeast

Trf1cDNA's in pGBT9 were transformed into yeast with pGAD10 containing no insert (Control), Tin2 Clone 1, Tin2 Clone 2 or fill-length Trf1. Interaction was assessed by a luminescent β-gal assay. For each pGBT9 construct control luminescence (interaction with insertless pGAD10 was 0.1–0.2 β-gal U and given the value of 1.

Figure 3:
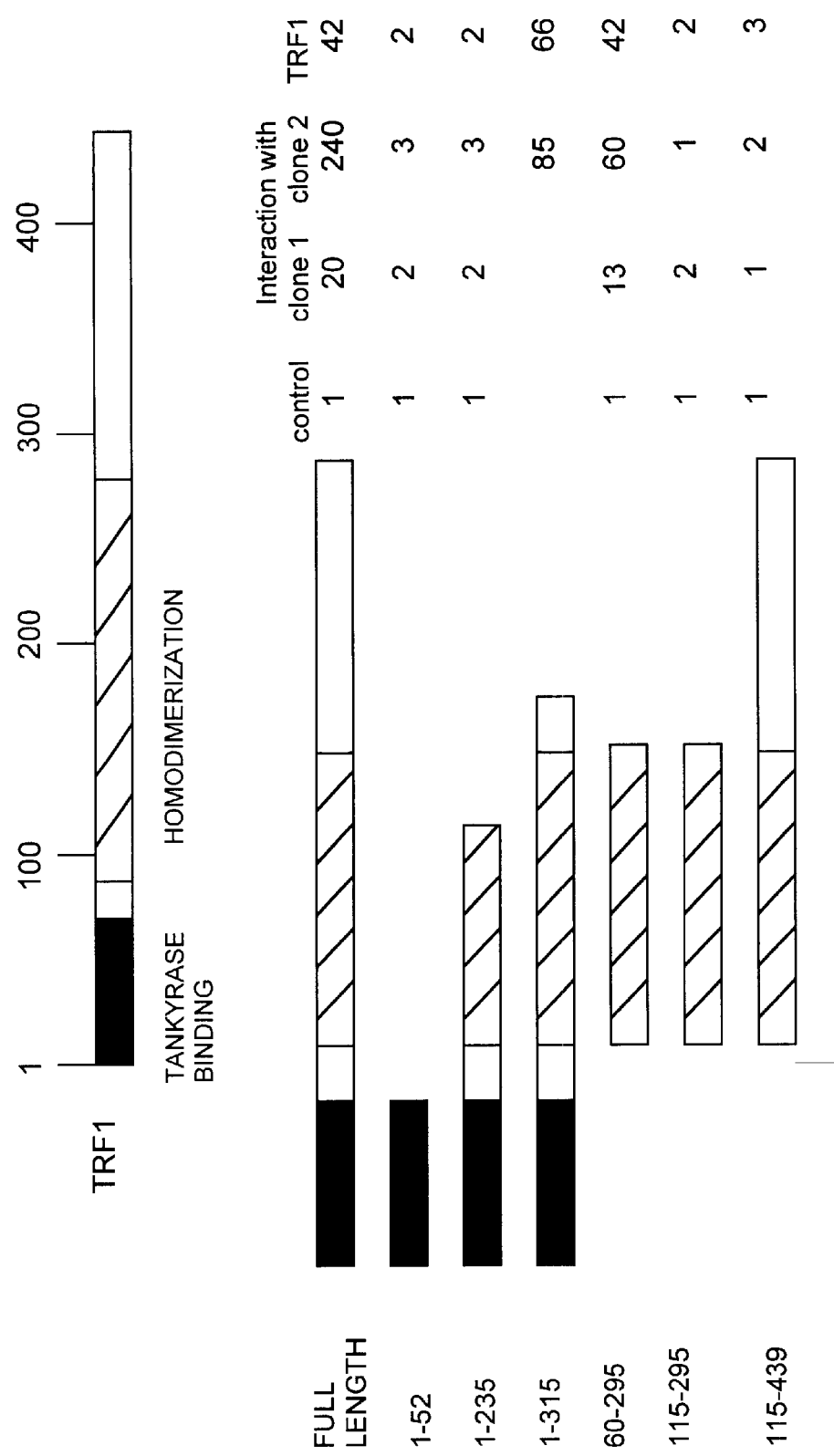
FIG. 3 shows the Trf1 domains that interact with Tin2; shown below the Trf1 protein drawing are the specific clones of Trf mutants and their interaction with various Tin2 clones.

To map the region in Trf1 that interacts with Tin2, interaction in yeast was tested using the Tin2 two-hybrid inserts and full or partial Trf1 cDNAs cloned in a complementary vector. The Trf1 protein constructs used and the results are shown in FIG. 3. In FIG. 3, the designation "Control" refers to level of activity produced by the Trf proteins shown on the left and a vector lacking an insert (i.e. producing no test protein). The Interaction Scores refers to relative intensity in the luminescent β-gal assay. There was no overlap between the region of Trf1 that binds tankyrase (Smith et al., 1998) and the Tin2-binding region (FIG. 3). Rather, Trf1 interacted with Tin2 via a central region that also contains the homodimerization domain (FIG. 3). Data described below suggest that Tin2 binding does not interfere with Trf1 dimerization. Thus, Trf1 may interact with Tin2 via a domain that is near, but does not overlap with, its homodimerization domain.

B. Epitope Tagging and Generation of Constructs

To verify the Tin2-Trf1 interaction, both proteins were epitope tagged at the N-terminus: Tin2 with a 13 aa c-Myc epitope (Myc-Tin2), and Trf1 with a 10 aa hemagglutinin epitope (HA-Trf1).

Myc-Tin2 (WT or mutant) cDNAs and HA-Trf1 cDNA were generated by PCR using appropriate primers to add the epitope tags, and cloned into pBluescriptII-SK (Stratagene) or pLXSN (Miller and Rosman, 1989). hTERT cDNA (human telomerase catalytic subunit, Counter et al., 1998) was cloned into pBabe-puro (Morganstern and Land, 1990). WT or mutant Tin2 cDNAs were cloned into pGex4X-1, and GST fusion proteins were expressed in $E.$ $coli$ and purified by glutathione-affinity chromatography, using a kit and protocols from Pharmacia. Baculoviruses carrying a 6his-Trf1 or 6his-Tin2 cDNA, or 6his -vector sequence (mock-infected controls), were constructed, produced and used to infect Sf9 cells, and proteins were purified by $Ni^{+2}$-chromatography, using a baculovirus expression kit and protocol from Pharmigen. Protein purity was assessed by SDS-PAGE.

The Myc-Tin2 (in pGEM-TA) and HA-Trf1 (in pBluescript II) cDNAs were transcribed from the T7 promoter, and translated with a rabbit reticulocyte lysate and $^{35}S$-methionine, using a commercial kit and protocols (Promega). Translation products were separated by SDS-PAGE using 4–15% gradient gels, and visualized by soaking the gel in 1 M Na salicylate (30 min) and exposing to X-ray film. GST or GST-fusion proteins (60 ng) were incubated with 5 nl in vitro translation reaction for 2 h at 4° C. 1 ng of anti-GST antibody (Santa Cruz Biotechnology) was added for 1 h. Alternatively, 5 nl of translation reactions, alone or mixed, were incubated with 1 ng anti-Myc (Invitrogen, R950-25) or anti-HA (Boehringer-Mannheim, 12CA5) antibodies for 1 h at 4° C. Immune complexes were collected on Protein A-sepharose beads, washed, released in 2X SDS-PAGE sample buffer, and analyzed by SDS-PAGE and autoradiography.

The Myc-Tin2 cDNA (which lacked the 5' UTR) directed the synthesis of a single protein that migrated slightly slower than unmodified Tin2. The HA-Trf1 cDNA directed the synthesis of a major protein with an apparent MW of 60 kD, as expected (Chong et al., 1995), and a faster-migrating species of ~40 kD that may be a degradation product. A Tin2 fusion protein was produced and purified from $E.$ $coli$ in which glutathione-S-transferase (GST) was linked to the N-terminus (GST-Tin2).

C. In vitro Immunoprecipitation

A series of experiments were conducted in which in-vitro translated Tin2 and Trf1 were produced as Myc-Tin2 and HA-Trf1 (Hemagglutinin) fusion proteins. These proteins were allowed to interact and were precipitated with anti-Myc or anti-HA antibodies. Precipitation complexes were analyzed with SDS-PAGE. Radiolabeled Myc-Tin2 and HA-Trf1 proteins were also produced by in vitro translation, and incubated with unlabeled GST-Tin2 or GST. GST complexes were immunoprecipitated, and the associated radiolabeled proteins were identified by SDS-PAGE. GST-Tin2, but not GST, co-precipitated the major (60 kD) and minor (40 kD) HA-Trf1 translation product. GST-Tin2 did not co-precipitate Myc-Tin2. These data suggest that Tin2 interacts with Trf1, but not with itself.

In vitro translated Myc-Tin2 and HA-Trf1 proteins were precipitated by anti-Myc and anti-HA antibodies, respectively, although anti-Myc was less efficient in this regard. When the in vitro translation products were incubated together prior to immunoprecipitation, anti-Myc precipitated both HA-Trf1 and Myc-Tin2 and anti-HA precipitated both HA-Trf1 and Myc-Tin2. Although the 40 kD HA-Trf1 species migrated near the position of Myc-Tin2, the two were distinguishable. These data support the conclusion that Tin2 interacts with Trf1.

D. Cell Culture Immunoprecipitation

Tin2 also interacted with Trf1 in cells. Myc-Tin2 and HA-Trf1 proteins were expressed in HT1080 human fibrosarcoma cells using amphotropic retroviruses. After selection for viral expression, cell lysates were immunoprecipitated and analyzed by western blotting for proteins in the immune complexes. In lysates from cells expressing both proteins, but not cells expressing either protein alone, the anti-Myc antibody precipitated HA-Trf1, and the anti-HA antibody precipitated Myc-Tin2.

Tin2 interacts with Trf1 in vitro and cells. Furthermore, Tin2, in contrast to Trf1 (Chong et al., 1995), did not form homotypic complexes, although it is possible that the GST moiety interferes with Tin2 homodimerization.

Example 3

Detection of Tin2 RNA in Various Tissues

The Tin2 cDNA hybridized to a single 2.4 kb species on northern blots of poly-A+ RNA from human heart, brain, placenta, lung, liver, skeletal muscle, kidney and pancreas, and total RNA from fetal lung or neonatal foreskin fibroblasts (WI-38, IMR-90 and HCA2). Proliferating, quiescent and senescent cells expressed similar levels of Tin2 mRNA, as did several immortal or tumorigenic cell lines (HMT-3522 non-tumorigenic breast epithelial cells, MDA-453 breast carcinoma, U2OS osteosarcoma, HTB9 bladder carcinoma, and C33A and HeLa cervical carcinoma [not shown]). Actin and QM DNA's were used as controls (Dimiri et al. 1996). Tin2 expression was similar in the non-tumorigenic breast cells, whether proliferating or confluent, compared to aggressive breast cancer cells. Thus, Tin2 appeared to be expressed by many, if not all, human tissues, and expression did not vary appreciably with growth state, immortalization or transformation.

Example 4

Subcellular Localization of Tin2 Determined by Immunofluorescence

HT1–80 cells were co-infected with HA-Trf1 and Myc-Tin2 retroviruses, fixed while growing or after treatment with colcemid, and immunostained with anti-HA or anti-Tin2 antibodies, and FITC-conjugated secondary antibody (green fluorescence) or biotinylated secondary antibody and Texas Red-conjugated streptavidin (red fluorescence).

The subcellular localization of retrovirally expressed Myc-Tin2 and HA-Trf1 was determined by immunofluorescence. As expected (Chong et al., 1995), anti-HA antibody localized Trf1 to small, randomly-distributed foci in interphase nuclei. Cells infected with a control virus showed no anti-HA staining. Anti-Myc antibodies failed to localize Myc-Tin2, despite their ability to detect the protein on western blots and localize other Myc-tagged proteins. Thus, the Myc-tag on Tin2 is inaccessible in cell nuclei. An affinity-purified polyclonal antibody against a C-terminal Tin2 fragment (aa 121–354) was produced. This antibody localized retrovirally expressed Tin2 to small randomly-distributed foci, most of which co-localized with Trf1 in interphase nuclei. Control cells showed barely detectable staining, consistent with the low level of endogenous Tin2. In mitotic nuclei, there was near complete concordance between Tin2 and Trf1 localization. Human metaphase chromosomes showed Tin2 predominantly at the telomeres, as reported for overexpressed Trf1 (Chong et al., 1995). Although weak Tin2 staining was sometimes observed along the chromosomes, the strongest signals were always at the ends. Thus, Tin2 associates with human telomeres.

Example 5

Tin2 mutants and their Effects in Telomerase Positive Cells

To determine the function of Tin2, four truncated mutants were created. Referring now to FIG. 4, there is shown the wild-type Tin2, having 354 amino acids, the N1(a1–120) N2(aa121–196) Trf-binding, and c-terminal domain (aa 276–354). The mutants were produced by standard molecular biological approaches, using PCR and/or restriction enzymes to remove portions of wt Tin2 cDNA. That is, the desired mutant was prepared by PCR, using appropriate primers to achieve the desired fragment. Three contained the Trf1-binding domain: Tin2–12, an N-terminal deletion of aa 1–120; Tin2–13, an N-terminal deletion of aa 1–196; Tin2–14, a C-terminal deletion of aa 276–354. The fourth mutant, Tin2–15, was an N-terminal fragment (aa 1–196) that lacked Trf1-binding and C-terminal domains.

Wild-type (WT) or mutant proteins were expressed in HT1080 cells, a telomerase-positive human tumor line, using retroviruses. Retroviruses carrying Tin2 cDNAs (wt or mutant) were used to deliver these cDNAs to the cells. The retroviruses integrate into the genome and the inserted cDNAs are then transcribed and translated. WT-Tin2 and Tin2–14 (C-terminal deletion) proteins were always highly expressed, whereas Tin2–12 (small N-terminal deletion) expression was variable. Tin2–13 (large N-terminal deletion) and Tin2–15 (N-terminal fragment) were always expressed at low levels, similar to that of endogenous Tin2, but nonetheless had biological activity (see below). Expression was stable over at least 20 population doublings (PD), and had no effect on cell growth or morphology. There was, however, a striking effect on telomere length.

Figure 5:
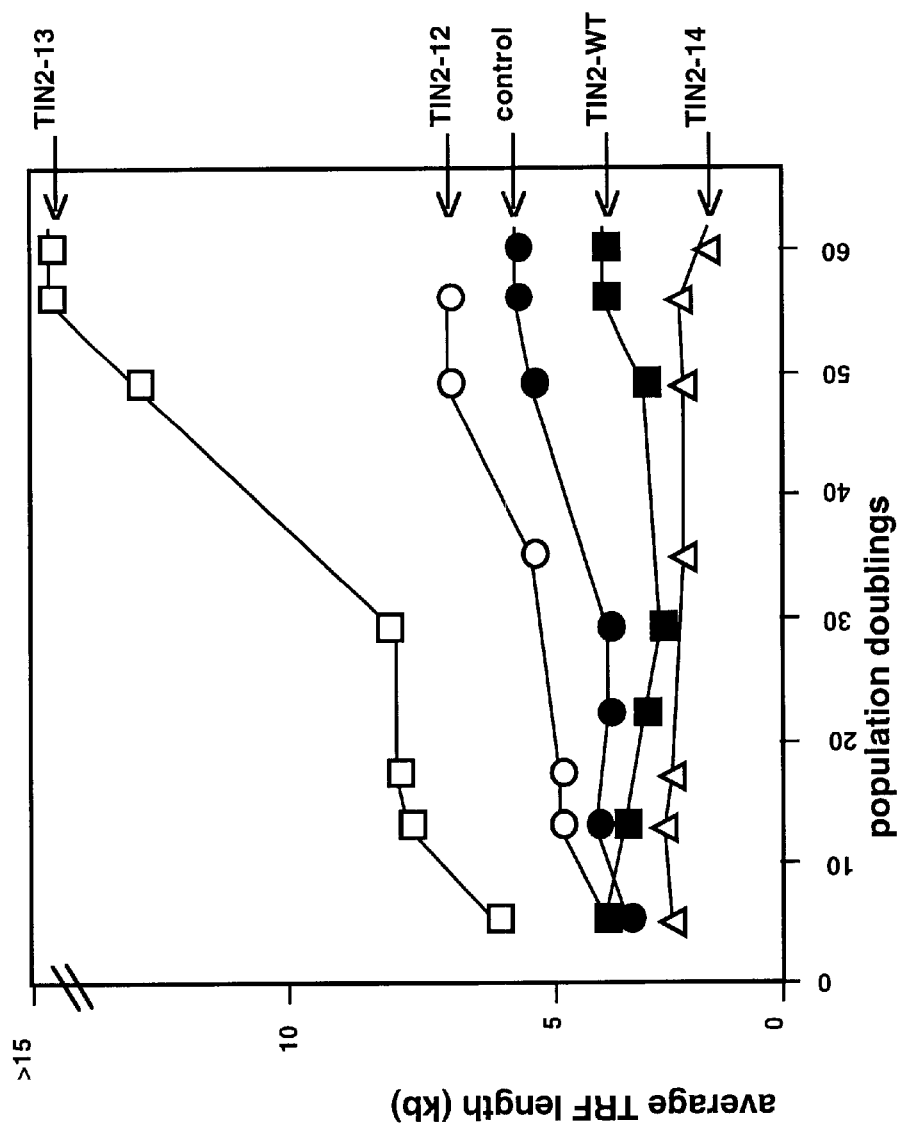
FIG. 5 shows the effects of Tin2 mutants on average telomere length (average telomere repeat factor length) in cell culture experiments.

HT1080 cells have relatively stable TRF lengths (Chong et al., 1995), maintained in our hands at 3–5 kb (closer to 5 kb after ~40 PD) (FIG. 5). Cells that overexpressed WT-Tin2 maintained an average TRF of 3 kb (FIG. 5), suggesting that Tin2 overexpression has no effect or slightly shortens the TRF. Tin2–14 (C-terminal deletion) overexpression also had little effect, slightly shortening the TRF to ~2 kb (FIG. 5). By contrast, Tin2–12, which retains Trf1-binding but lacks 120 N-terminal aa, increased the TRF to 6–7 kb. Tin2–13, which retains Trf1-binding but lacks 196 N-terminal aa, had a more striking effect, increasing the TRF to ~15 kb (FIG. 5). Similarly, Tin2–15, the N-terminal fragment, increased the TRF to 10–12 kb. Thus, Tin2 mutants that either lack N-terminal domains or contain only the N-terminus increased telomere length. Telomere elongation was evident within 5 PD, but was maximal after ~50 PD.

Telomere elongation by N-terminal deleted Tin2 was telomerase-dependent. WT- or Tin2–13 proteins were expressed in normal human fibroblasts (WI-38), which senesce at ~50 PD and do not express telomerase. Neither protein induced telomerase activity, or altered replicative life span or TRF length. This was not the case when the cells were rendered telomerase positive by (a retrovirus carrying hTERT, the catalytic subunit of human telomerase (Weinrich et al., 1997; Counter et al., 1998). This retrovirus was produced by cloning hTERT cDNA into the retroviral vector. hTERT expression induced telomerase activity, retarded telomere shortening and extended replicative life span, as expected. Co-expression of hTERT and WT-Tin2 had no effect or slightly shortened the TRF over 10–15 PD. By contrast, co-expression of hTERT and Tin2–13 increased the TRF to >10 kb. This increase persisted for at least 25 PD.

The results suggest that Tin2 negatively regulates telomerase, and Tin2–13 interferes with wild-type Tin2 function. When a mutant gives a phenotype (i.e. long telomeres) it is presumed that the wild type does the opposite. Since Tin2–13 elongates telomeres, we presume that wt Tin2 prevents telomere elongation. Since wt Tin2 did not inhibit telomerase activity in vitro we presume Tin2 acts indirectly. This regulation appeared to be indirect. An HA-tagged hTERT protein (Meyerson et al., 1998), transiently expressed in Myc-Tin2-expressing cells, did not co-immunoprecipitate Myc-Tin2. Moreover, wild-type or mutant GST-Tin2 proteins had no effect on telomerase (TRAP) activity in vitro. Tin2 may recruit factors that inhibit telomerase, or induce a protein-DNA structure that limits telomerase access.

Example 6

Tin2 Interactions with DNA, and Trf1-telomeric DNA Complex

Tin2 did not bind DNA in electrophoretic mobility shift assays (EMSA) using a double-stranded $[TTAGGG]_{13}$ probe. This was true whether Tin2 was translated in vitro, purified from *E. coli* as a GST-fusion protein, or purified from baculovirus infected insect cells as a 6-histidine (6his)-tagged protein. Although it is possible that DNA binding requires a modification that did not occur in vitro or in these cells, the results suggest that Tin2 does not bind telomeric DNA directly. In contrast, Trf1, whether translated in vitro or in nuclear extracts from HA-Trf1 overexpressing cells, formed a specific protein-DNA complex (Chong et al., 1995). Since Trf1 binds DNA as a homodimer (Bianchi et al., 1997), this complex was designated TT. To determine whether Tin2 interacts with this complex, WT or mutant GST-Tin2 proteins were added to nuclear extracts from HA-Trf1 expressing cells. Because GST-Tin2 alone does not bind the probe, mobility shifts in TT are likely due to an interaction between Tin2 and Trf1.

GST-Tin2–15, which cannot bind Trf1, did not alter the mobility of TT. By contrast, GST-Tin2–13, which binds Trf1 but lacks 196 N-terminal aa, shifted TT into two larger complexes. These complexes, designated TT-A and TT-AA, which were disrupted by anti-GST and anti-HA antibodies, likely consist of a Trf1 homodimer and one (TT-A) or two (TT-AA) Tin2 molecules. Since homodimerization is required for Trf1 DNA binding (Bianchi et al., 1997), this result suggests that Tin2 binding per se does not disrupt Trf1 dimerization. GST-Tin2–12 and GST-Tin2–14, which bind Trf1 but lack N- or C-terminal residues, also shifted TT into TT-A and TT-AA, although they were less efficient than Tin2–13. Thus, Tin2 mutant proteins that bind Trf1 shifted TT into TT-A and TT-AA complexes.

Wild-type GST-Tin2 also shifted TT into the higher molecular weight band TT-AA, but formed an additional, larger complex designated TT-AAX that was disrupted by anti-Tin2 antibody. As with previous designations, "TT" refers to 2 Trf1 molecules and "AA" refers to 2 Tin2 molecules. "X" refers to an unknown molecule. Low levels of GST-Tin2 partially depleted TT, forming a small amount of TT-AAX, whereas higher levels completely depleted TT, forming more TT-AAX. In either case, the amount of TT-AA and TT-AAX formed by GST-Tin2 was much less than the starting amount of TT. This suggests that the GST moiety, or binding or EMSA conditions, may be suboptimal for TT-AAX formation/stability. Whatever the case, TT-AAX formation was a property of WT-Tin 2, and to a lesser extent Tin2–14, and depended on Trf1 binding and the N-terminus. TT-AAX may consist of Trf1, Tin2, and additional nuclear proteins bound to the probe. Alternatively, TT-AAX may consist of probes bound by Tin2/Trf1 multimers, or probe clusters held together by Tin2 and Trf1.

To determine the nature of TT-AAX, DNA complexes formed by purified proteins were examined. 6his-tagged Trf1 and Tin2 were produced and purified from baculovirus-infected cells. 6his-Trf1 formed a single TT complex, and 6his-Tin2 did not bind DNA. Moreover, 6his-Tin2, added in increasing amounts to 6his-Trf1 and probe, shifted all the TT to TT-AAX . Since 6his-Tin2 formed more TT-AAX than GST-Tin2, the GST moiety may reduce TT-AAX formation or stability. Nuclear extract had only a small effect on TT-AAX formation. Extract alone showed no specific binding, consistent with the low levels of endogenous Trf1 (Chong et al., 1995) and Tin 2. Addition of 6his-Trf1 produced TT, and 6his-Tin2 shifted all the TT to TT-AAX. However, somewhat more TT-AAX was formed in the presence of nuclear extract than its absence. Thus, TT-AAX required only Trf1, Tin2 and telomeric DNA, but other nuclear proteins might enhance its formation or stability.

Example 7

Telomere DNA Clustering

To determine whether Tin2 promotes probe clustering, two [TTAGGG]$_6$ probes were synthesized that differed in the lengths of the flanking sequence. The 178 bp probe (6X-Tel) and the 126 bp probe (Bi-6X-Tel) were used either labeled or unlabeled. The probes were mixed together, incubated with purified 6his-proteins under optimized conditions, and Bi-6X-Tel probes were collected on streptavidin-agarose beads, as described below. Phenol extraction, which does not disrupt biotin-streptavidin binding, was used to release 6X-Tel and Bi-6X-Tel probes that were bound to the streptavidin-Bi-6X-Tel complex owing to protein-protein or protein-DNA interactions. Released labeled probes were identified by PAGE.

6his-Trf1 (150 ng) and increasing amounts of 6his-Tin2 were incubated with a double stranded TTAGGG$_6$ probe, and protein-DNA complexes were analyzed by EMSA. Probes containing [TTAGGG]$_6$ and flanking sequences were synthesized by PCR. 6X-Tel was 178 bp, and labeled with $^{32}$P (*). Bi-6X-Tel was 126 bp, biotinylated at a 5' end, and either labeled (*) or unlabeled. The 6X-Tel probe was incubated with labeled or unlabeled Bi-6X-Tel probe, and 6his-Trf1 (150 ng), 6his-Tin2 (60 ng), GST (100 ng), GST-Tin2–13 (100 ng) and/or 100 fold excess unlabeled [TTAGGG]$_7$, followed by incubation with streptavidin-agarose beads. The beads were collected, and components released and analyzed by PAGE. Signals were quantified using a phosphorimager and ImageQuant. Reaction mixtures were analyzed by EMSA.

In the absence of protein or presence of Tin 2 alone, virtually no 6X-Tel probe, and very little labeled Bi-6X-Tel was released. Thus, the probes did not associate with each other under these conditions. Trf1 alone increased the amount of both 6X-Tel and labeled Bi-6X-Tel that were released. These results suggest that Trf1 alone induced probe-probe interactions (6X-Tel/Bi-6X-Tel, and Bi-6X-Tel/Bi-6X-Tel), consistent with finding that Trf1 promotes telomeric DNA pairing (Griffith et al., 1998). Tin2 markedly stimulated the probe interactions induced by Trf1. Tin2 stimulated the 6X-Tel/labeled Bi-6X-Tel interaction 9- to 10-fold, and the 6X-Tel/unlabeled Bi-6X-Tel interaction 4- to 5-fold, over the activity of Trf1 alone. The probe interactions stimulated by Tin2 depended on the telomeric sequence, because the signal was abolished by excess unlabeled [TTAGGG]$_7$. The [TTAGGG]$_7$ was used to compete with [TTAGGG]$_6$ for binding in this study. The N-terminal deletion mutant Tin2–13 was 9- to 10-fold less active than wild-type Tin2 in promoting interaction among the probes.

EMSA confirmed that the probes formed TT with purified Trf1 and did not form a complex with Tin2. Under these optimized conditions, Trf1 alone formed a small amount of TT-AAX which was greatly stimulated by Tin2. Also under these conditions, Trf1 alone formed two minor complexes that are likely due to two (TT) and three (TT*) Trf1 homodimers loaded onto the probe (Bianchi et al., 1997). The Tin2–13 mutant supershifted all three TT complexes, as expected from its ability to bind Tfr1.

These results demonstrate that Tin2 facilitates pairing or clustering of telomeric DNA tracts. This activity was deficient in Tin2–13, which elongated telomeres in vivo. Thus, Tin2 promotes a compact telomeric structure that limits telomerase access to the telomere.

Example 8

Antibodies

Antibodies including both polyclonal and monoclonal antibodies, and drugs that modulate the production or activity of TIN2 and/or its subunits possess certain diagnostic applications and may for example, be utilized for the purpose of detecting and/or measuring conditions such as cell senescence, immortality or the like. For example, Tin2 may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of Tin2 of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against Tin2 peptides can be screened for various properties; i.e., isotype, epitope, affinity, etc. Of particular interest are monoclonal antibodies that neutralize the binding activity of Tin2 or its subunits. Such monoclonals can be readily identified in, for example, gel-shift assays. High affinity antibodies are also useful when immunoaffinity purification of native or recombinant Tin2 is possible.

Additionally, spleen cells can be harvested from the immunized animal (typically rat or mouse) and fused to myeloma cells to produce a bank of monoclonal antibody-secreting hybridoma cells. The bank of hybridomas can be screened for clones that secrete immunoglobulins that bind the protein of interest specifically, i.e., with an affinity of at least $1 \times 10^7$ M$^{-1}$. Animals other than mice and rats may be used to raise antibodies; for example, goats, rabbits, sheep, and chickens may also be employed to raise antibodies reactive with a Tin2 protein. Transgenic mice having the capacity to produce substantially human antibodies also may be immunized and used for a source of antiserum Land/or for making monoclonal antibody secreting hybridomas.

Thus, the invention provides polyclonal and monoclonal antibodies that specifically bind to Tin2 protein. Bacteriophage antibody display libraries may also be screened for phage able to bind peptides and proteins of the invention specifically. Combinatorial libraries of antibodies have been generated in bacteriophage lambda expression systems and may be screened as bacteriophage plaques or as colonies of lysogens. For general methods to prepare antibodies, see Antibodies: A Laboratory Manual (1988), E. Harlow and D. LANE, Cold Spring Harbor Laboratory, Cold Spring Harbor, N.Y., incorporated herein by reference.

These antibodies can in turn be used to isolate Tin2 proteins from normal or recombinant cells and so can be used to purify the proteins as well as other proteins associated therewith. Such antibodies are useful in the detection of Tin2 proteins in samples and in the detection of cells comprising Tin2 proteins in complex mixtures of cells. Such detection methods have application in screening, diagnosing, and monitoring diseases and other conditions, such as cancer, pregnancy, or fertility, because the Tin2 proteins are present in most cells capable of elongating telomeric DNA and expressing telomerase activity and are present in those cells at levels significantly higher than the levels observed in telomerase negative cells.

For some applications of the antibodies of the invention, such as identifying immuno-crossreactive proteins, the desired antiserum or monoclonal antibody(ies) is/are not monospecific. In these or other instances, it may be preferable to use a synthetic or recombinant fragment of a Tin2 protein as an antigen rather than the entire protein. More specifically, where the object is to identify immuno-crossreactive polypeptides that comprise a particular structural moiety, such as a DNA-binding domain, it is preferable to use as an antigen a fragment corresponding to part or all of a commensurate structural domain in the Tin2 protein.

Example 9

Drug Screening

In addition to rational design of agonists and antagonists based on the structure of the Tin2-TRF binding domain and Tin2 telomeric tract activity, the present invention further contemplates an alternative method for identifying specific antagonists or agonists using various screening assays known in the art.

Accordingly any screening technique known in the art can be used to screen for agonists or antagonists of the Tin2 binding domain. The present invention contemplates screens for small molecule ligands or ligand analogs and mimics, as well as screens for natural ligands that bind to and agonize or antagonize Tin2 binding in vivo. For example, natural products libraries can be screened using assays of the invention for molecules that agonize or antagonize TRF dimerization activity.

Knowledge of the primary sequence of the various Tin2 domains, and the similarity of that sequence with domains contained in other proteins, can provide an initial clue to inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" Scott and Smith, 1990, Science 249: 386–390 (1990); Cwirla, et al., Proc. Natl. Acad. Sci., 87: 6378–6382 (1990); Devlin et al., Science, 249: 404–406 (1990). very large libraries can be constructed . A second approach uses primarily chemical methods, of which the Geysen method, Geysen et al., Molecular Immunology 23: 709–715 (1986); Geysen et al. J. Immunologic Method 102: 259–274 (1987),and the method of Fodor et al. Science 251: 767–773 (1991) are examples. Houghton U.S. Pat. No. 4,631,211, issued December 1986, and Rutter et al. U.S. Pat. No. 5,010,175, issued Apr. 23, 1991 describe methods to produce a mixture of peptides that can be tested as agonists or antagonists.

In another aspect, synthetic libraries, Needels et al., Proc. Natl. Acad. Sci. USA 90: 10700–4 (1993); Ohlmeyer et al., Proc. Natl. Acad. Sci. USA 90: 10922–10926 (1993); Lam et al., International Patent Publication WO 92/00252; Kocis et al., International Patent Publication No. WO 9428028 each of which is incorporated herein by reference in its entirety, and the like can be used to screen for ligands to the Tin2 binding domain(s) according to the present invention.

Alternatively, assays for binding of soluble ligands to cells that express recombinant forms of Tin2 can be performed. The soluble ligands can be provided readily as recombinant or synthetic polypeptides.

The screening can be performed with recombinant cells that express Tin2, or fragment thereof, or alternatively, using purified protein, e.g., produced recombinantly, as described above. For example, the ability of labeled, soluble or solubilized Tin2 to bind ligand can be used to screen libraries, as described in the foregoing references.

In one such example, a phage library can be employed. Phage libraries have been constructed which when infected into host *E. coli* produce random peptide sequences of approximately 10 to 15 amino acids, Parmley and Smith, Gene, 73: 305–318 (1988), Scott and Smith, Science, 249: 386–249 (1990). Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of Tin2. After a specified incubation period, the filters can be thoroughly washed and developed for autoradiography.

Plaques containing the phage that bind to the radioactive binding domain can then be identified. These phages can be further cloned and then retested for their ability to hinder the formation of Tin2-TRF and/or the binding of TRF to its telomere repeat sequence. Once the phages have been purified, the binding sequence contained within the phage can be determined by standard DNA sequencing techniques. Once the DNA sequence is known, synthetic peptides can be generated which represent these sequences.

In an alternative embodiment, the radioactive Tin2 fragment can contain the TRF binding domain. Plaques containing the phage that bind to the radioactive binding domain can be identified, further cloned and retested for their ability to hinder the binding of TRF to its telomere repeat sequence. Again, once the phages have been purified, the binding sequence contained within the phage can be determined by standard DNA sequencing techniques. Once the DNA sequence is known, synthetic peptides can be generated which represent these sequences.

These peptides can be tested, for example, for their ability to: (1) interfere with TRF forming a Tin2 heterodimer; and/or (2) interfere with TRF binding to its telomere repeat sequence and or (3) modulate Tin2 activity in aligning telomeric DNA tracts. If the peptide interferes in the second case, but does not interfere in the first case, it may be concluded that the peptide interferes with the TRF homodimer binding to its telomere repeat sequence.

The effective peptide(s) can be synthesized in large quantities for use in in-vivo models and eventually in humans to stimulate or inhibit telomere elongation. Synthetic peptide production is relatively non-labor intensive, easily manufactured, quality controlled and thus, large quantities of the desired product can be produced quite cheaply. Similar combinations of mass produced synthetic peptides have recently been used with great success. Patarroyo, Vaccine, 10: 175–178 (1990).

Example 10

Tin2 Assay

A test kit may be prepared for the demonstration of the presence or capability of materials for binding activity to Tin2, comprising:

(a) a predetermined amount of at least one labeled immunochemically reactive component obtained by the direct or indirect attachment of the present Tin2 or a specific binding partner thereto, to a detectable label;

(b) other reagents; and (c) directions for use of said kit.

More specifically, the diagnostic test kit may comprise:

(a) a known amount of the Tin2 as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the Tin2 to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the TIN2 and a specific binding partner thereto.

In accordance with the above, an assay system for screening potential drugs effective to modulate the activity of the Tin2 may be prepared. The Tin2 may be introduced into a test system, and the prospective drug may also be introduced into the resulting cell culture, and the culture thereafter examined to observe any changes in the telomere lengths of chromosomes in the cells, due either to the addition of the prospective drug alone, or due to the effect of added quantities of the known Tin2.

Example 11

Tin2 From Other Species

5' and 3' race cDNA library which was constructed from the testis cDNA of Mus musculis was obtained from Clontech, Inc., and probed for the mouse Tin2 full length of cDNA. The GenBank dbEST database was searched with the previously cloned full length human Tin2 cDNA. The Tin2 cDNA sequence was the query sequence. Using a BLAST search, a mouse EST cDNA was identified. This sequence was used to design primers for 5' and 3' race PCR amplification of the proper sequence from the mouse cDNA library. The mouse DNA Tin2 sequence is described in SEQ ID NO. 3, while the mouse protein sequence is in SEQ ID NO. 4.

The mouse Tin2 shared various regions of homology with the human sequence. In the acidic/basic region, the two proteins share 77% homology; in the TRF1 binding region, they share 60% homology; in the C-terminal region they share 43% homology. Homology is calculated using standard programs in the MacVector molecular biology suite from Oxford Molecular.

The mouse sequence may be modified by selective PCR amplification to create various deletion mutants, as previously described. It may also, like the human sequence, be mutated by techniques such as site directed mutagenesis. Furthermore, the mouse sequence may be inserted into transgenic mice or deleted in knock-out mice, as is known in the art.

References cited in Specification

Aparicio, O. M., Billington, B. L., and Gottschling, D. E. (1995). Modifiers of position effect are shared between telomeric and silent mating-type loci in S. cerevisiae. Cell 66, 1279–1287.

Bianchi, A., Smith, S., Chong, L., Elias, P., and de Lange, T. (1997) TRF1 is a dimer and bends telomeric DNA. EMBO J 16, 1785–1794.

Blackburn, E. H. (1991). Structure and function of telomeres. Nature 350, 569–573.

Bodnar, A. G., Ouellette, M., Frolkis, M., Holt, S. E., Chiu, C. P., Morin, G. B., Harley, C. B., Shay, J. W., Lichtsteiner, S., and Wright, W. E. (1998). Extension of life span by introduction of telomerase into normal human cells. Science 279, 349–352.

Brachmann, C. B., Sherman, J. M., Devine, S. E., Cameron, E. E., Pillus, L., and Brocke, J. D. (1995). The SIR2 gene family, conserved from bacteria to humans, function in silencing, cell cycle progression and chromosome stability. Genes & Dev. 9, 2888–2902.

Briand, P., Petersen, O. W., and van Deurs, B. (1987). A new diploid nontumorigenic human breast epithelial cell line isolated and propagated in a chemically defined medium. In Vitro Cell Dev. Bio. 23: 181–188.

Bryan, T. M., Englezou, A., Dalla-Pozza, L., Dunham, M. A., and Reddel, R. (1997). Evidence for an alternative mechanism for maintaining telomere length in human tumors and tumor-derived cell lines. Nature Med. 3, 1271–1274.

Campisi J. (1996). Replicative senescence: An old lives tale? Cell 84, 497–500.

Campisi, J., Dimri, G. P., and Hara, E. (1996). Control of replicative senescence. In: Handbook of the Biology of Aging. Schneider, E., and Rowe, J., eds. Academic Press, New York, pp. 121–149.

Campisi J. (1997). The biology of replicative senescence. Europ. J. Cancer 33, 703–709.

Chien, C.T., Bartel, P. L., Sternglanz, R., and Fields, S. (1991). The two-hybrid system: A method to identify and clone genes for proteins that interact with a protein of interest. Proc. Nat'l Acad. Sci 88, 9578–9582.

Chong, L., van Steensel, B., Broccoli, D., Erdjument-Briomage, H., Hanish, J., Tempst, P., and de Lange, T. (1995). A human telomeric protein. Science 270, 1663–1667.

Cockell, M., Palladino, F., Laroche, T., Kyrion, G., Liu, C., Lustig, A. J., and Gasser, S. M. (1995). The carboxy termini of Sir4 and Rap1 affect Sir3 localization: evidence for a multicomponent complex required for yeast telomeric silencing. J. Cell Biol. 129, 909–924.

Conrad, M. N., Wright, J. H., Wolf, A. J., and Zakian, V. A. (1990). RAP1 protein interacts with yeast telomeres in vivo: Overproduction alters telomere structure and decreases chromosome stability. Cell 63, 739–750.

Compton, D. A., Yen, T. J., and Cleveland, D. W. (1991) Identification of a novel centromere/kinetochore-associated protein using monoclonal antibodies generated against human mitotic chromosome scaffolds. J. Cell Bio. 112, 1083–1097.

Cooper, J. P., Watanabe, Y., and Nurse, P. (1998) Fission yeast Taz1 protein is required for meiotic telomere clustering and recombination. Nature 392, 828–831.

Counter C. M., Hahn, W. C., Caddle, S. D., Beijersbergen, R. L., Lansdorp, P. M., Sedivy, J. M., and Weinberg, R. A., (1998). Dissociation among in vitro telomerase activity, telomere maintenance, and cellular immortalization. Proc. Natl. Acad. Sci. USA 95, 14723–14728.

Dimri, G. P., Hara, E., and Campisi, J. (1994). Regulation of two E2F-related genes in presenescent and senescent human fibroblasts. J. Biol. Chem. 269, 16180–16186.

Dimri G. P., Lee, X., Basile, G., Acosta, M., Scott, G., Roskelley, C., Medrano, E. E., Linskens, M., Rubelj, I., Pereira-Smith, O., Peacocke, M., and Campisi, J. (1995). A novel biomarker identifies senescent human cells in culture and aging skin in vivo. Proc. Nat'l Acad. Sci. USA 92, 9363–9367.

Dimri, G. P., Testori, A., Acosta, M., and Campisi, J. (1996) Replicative senescence, aging and growth regulatory transcription factors. Biol. Signals 5, 154–162.

Finer, M. H., Dull, T. J., Qin, L., Farson, D., and Roberts, M. R. (1994) kat: A high-efficiency retroviral transduction system for primary human T lymphocytes. Blood 83, 43–50.

Grandin, N., Reed, S. I., and Charbonneau, M. (1997). Stn1, a new Saccharomyces cerevisiae protein, is implicated in telomere size regulation in association with Cdc13. Genes & Dev. 11, 512–527.

Greider, C. W. (1996). Telomere length regulation. Annu. Rev. Biochem. 65, 337–365.

Griffith, J., Bianchi, A., and de Lange, T. (1998). TRF1 promotes parallel pairing of telomeric tracts in vitro. J Mol. Bio. 278, 79–88.

Hardy, C. F., Sussel, L., and Shore, D. (1992). A RAP1-interacting protein involved in transcriptional silencing and telomere length regulation. Genes & Dev. 6, 801–814.

Harley, C. B., Futcher, A. B., and Greider, C. W. (1990). Telomeres shorten during aging of human fibroblasts. Nature 345, 458–460.

Harley, C. B., and Villeponteau, B. (1995). Telomeres and telomerase in aging and cancer. Curr. Opin. Genet. Dev. 5, 249–255.

James, P., Halladay, J., and Craig, E. A. (1996). Genomic libraries and a host-strain designed for highly efficient two-hybrid selection in yeast. Genetics 144: 1425–1436.

Kim, N. W., Piatyszek, M. A., Prowse, K. R., Harley, C. B., West, M. D., Ho, P. L. C., Coviello, G. M., Wright, W. E., Weinrich, and S. L., Shay, J. W. (1994). Specific association of human telomerase activity with immortal cells and cancer. Science 266, 2011–2015.

Kiyono, T., Foster, S. A., Koop, J. I., McDougall, J. K., Galloway, D. A., and Klingelhutz, A. J. (1998). Both Rb/pl6lNK4a inactivation and telomerase activity are required to immortalize human epithelial cells. Nature 396, 84–88.

Kyrion, G., Boakye, K. A., and Lustig, A. J. (1992). C-terminal truncation of RAP1 results in the deregulation of telomere size, stability, and function in Saccharomyces cerevisiae. Molec. Cell. Biol. 12, 5159–5173.

Levy, M. Z., Allsopp, R. C., Futcher, A. B., Greider, and C. W., Harley, C. B. (1992). Telomere end-replication problem and cell aging. J. Molec. Biol. 225, 951–960.

Lingner, J., and Cech, TR. (1998). Telomerase and chromosome end maintenance. Curr. Opin. Genet. Dev. 8, 226–232.

Marchand, S., Buck, S. W., Moretti, P., Gilson, E., and Shore, D. (1996). Silencing of genes at nontelomeric sites in yeast is controlled by sequestration of silencing factors at telomeres by Rap1 protein. Genes & Dev. 10, 1297–1309.

Meyerson, M., Counter, C. M., Eaton, E. N., Ellisen, L. W., Steiner, P., Caddle, S. D., Ziaugra, L., Beijersbergen, R. L., Davidoff, M. J., Liu, Q., Bacchetti, S., Haber, D. A., and Weinberg, R. A. (1997). hEST2, the putative human telomerase catalytic subunit gene, is upregulated in tumor cells and during immortalization. Cell 90, 785–795.

Miller, A. D., and Rosman, G. J. (1989). Improved retroviral vectors for gene transfer and expression. BioTechniques 7, 980–988.

Morgenstern, J. P., and Land, H. (1990). Advanced mammalian gene transfer: high titre retroviral vectors with multiple drug selection markers and a complementary helper-free packaging cell line. Nucl. Acids Res. 18, 3587–3596.

Nugent, C. I., Hughes, T. R., Lue, N. F., and Lundblad, V. (1996). Cdc13p: a single-strand telomeric DNA binding protein with a dual role in yeast telomere maintenance. Science 274, 249–252.

Nugent, C. I., and Lundblad, V. (1998). The telomerase reverse transcriptase: components and regulation. Genes & Dev. 12, 1073–1085.

Sager, R. (1991). Senescence as a mode of tumor suppression. Environ. Health Persp. 93, 59–62.

Sambrook, J., Fritch, E. F., Maniatis, T. (1989). Molecular cloning. Cold Spring Harbor Press, New York.

Shay, J. W., and Wright, W. R. (1991). Defining the molecular mechanisms of human cell immortalization. Biochim. Biophys. Acta 1071, 1–7.

Shen, M., Haggblom, C., Vogt, M., Hunter, T., and Lu, K. P. (1997). Characterization and cell cycle regulation of the related telomeric proteins Pin2 and TRF1 suggest a role in mitosis. Proc. Nat'l Acad. Sci. USA 94, 13618–13623.

Shore, D. (1997). Telomerase and telomere-binding proteins: controlling the end game. Trends Biochem. Sci. 22, 233–235.

Smith, S., Giriat, I., Schmitt, A., and de Lange, T. (1998). Tankyrase, a poly (ADP-ribose) polymerase at human telomeres. Science 282, 1484–1487.

van Steensel, B., and de Lange, T. (1997). Control of telomere length by the human telomeric protein TRF1. Nature 385, 740–743.

van Steensel, B., Smogorzewska, A., and de Lange, T. (1998). TRF2 protects human telomeres from end to end fusions. Cell 92, 401–413.

Vaziri, H., and Benchimol, S. (1998). Reconstitution of telomerase activity in normal human cells leads to elongation of telomeres and extended replicative life span. Curr. Biol. 8, 279–282.

Weinberg, R. A. (1991). Tumor suppressor genes. Science 254,1138–1146. Weinrich, S. L., Pruzan, R., Ma, L., Ouellette, M., Tesmer, V. M., Holt, S. E., Bodnar, A. G., Lichsteiner, S., Kim, N. W., Trager, J. R., Taylor, R. D., Carlos, R., Andrews, W. H., Wright, W. E., Shay, J. W., Harley, C. B., and Morin, G. B. (1997). Reconstitution of human telomerase with the template RNA component hTR and the catalytic protein subunit hTRT. Nature Genet. 17, 498–502.

Wotton, D., and Shore, D. (1997). A novel Rap1p-interacting factor, Rif2p, cooperates with Rif1p to regulate telomere length in Saccharomyces cerevisiae. Genes & Dev. 11, 748–760.

Yeager, T. R., DeVries, S., Jarrard, D. F., Kao, C., Nakada, S. Y., Moon, T. D., Bruskewitz, R., Stadler, W., Meisner, L. F. F., Gilchrist, K. W., Newton, M. A., Waldman, F. B., and Reznikoff, C. A. (1998). Overcoming cellular senescence in human cancer pathogenesis. Genes & Dev. 12, 163–74.

Zakian, V. A. (1989). Structure and function of telomeres. Annu. Rev. Genet. 23, 579–604. Zhong, Z., Shiue, L., Kaplan, S, and de Lange, T. (1992). A mammalian factor that binds telomeric TTAGGG repeats in vitro. Molec. Cell. Bio. 12, 4834–4843.

What is claimed is:

1. An isolated polynucleotide encoding a Tin2 protein, said polynucleotide having a sequence selected from the group consisting of:
   a. SEQ ID NO: 1;
   b. SEQ ID NO: 3;
   c. the sequence of SEQ ID NO: 1 beginning at nucleotide 623 (Tin 2–12);
   d. the sequence of SEQ ID NO: 1 beginning at nucleotide 903 (Tin 2–13);
   e. the sequence of SEQ ID NO: 1 from nucleotide 263 to nulcleotide 1089 (Tin 2–14);
   f. the sequence of SEQ ID NO: 1 from nucleotide 263 to nucleotide 902 (Tin 2–15); and
   g. a sequence fully complementary to a sequence as recited in one of (a)–(f) above.

2. A vector for expressing a Tin2 protein comprising the Tin2 polynucleotide of claim 1.

3. A host cell transformed with the vector of claim 2.

4. An isolated polynucleotide which encodes a protein consisting essentially of the amino acid sequence of SEQ ID NO: 2.

5. An isolated polynucleotide having a sequence fully complementary to the polynucleotyide of claim 4.

6. An isolated polynucleotide which encodes a protein consisting essentially of the amino acid sequence of SEQ ID NO: 4.

7. An isolated polynucleotide having a sequence fully complementary to the polynucleotide of claim 6.

8. An isolated polynucleotide which encodes a Tin2 protein consisting essentially of an amino acid sequence selected from the group consisting of: tin2–12; Tin 2–13; Tin 2–14; and Tin 2 . 15,
   wherein Tin2–12 has amino acids 121–354 of SEQ ID NO: 2;
   wherein Tin2–13 has amino acids 197–354 of SEQ ID NO: 2;
   wherein Tin2–14 has amino acids 1–275 of SEQ ID NO: 2; and
   wherein Tin2–15 has amino acids 1–196 of SEQ ID NO: 2.

9. An isolated polynucleotide having a sequence fully complementary to the polynucleotide of claim 8.

10. A method for producing Tin2 protein comprising expressing protein from an isolated polynucleotide, said polynuceotide selected from the group consisting of:

a. SEQ ID NO: 1;
b. SEQ ID NO: 3;
c. Tin2–12 having a polynucleotide sequence from nucleotides 623–1324 of SEQ ID NO: 1;
d. Tin 2–13 having a polynucleotide sequence from nucleotides 903–1324 of SEQ ID NO: 1;
e. Tin 2–14 having a polynucleotide sequence from nucleotides 263–1089 of SEQ ID NO: 1; and
f. Tin 2–15 having a polynulceotide sequence from nucleotides 263–902 of SEQ ID NO: 1.

* * * * *

UNITED STATES PATENT AND TRADEMARK OFFICE
CERTIFICATE OF CORRECTION

PATENT NO.        : 6,409,648 B1                             Page 1 of 1
APPLICATION NO.   : 09/608917
DATED             : June 25, 2002
INVENTOR(S)       : Sahn-Ho Kim and Judith Campisi It is certified that error appears in the above-identified patent and that said Letters Patent is hereby corrected as shown below:

On the first page of the specification in the second paragraph of the section entitled:

GOVERNMENT RIGHTS after "This invention was made during work supported by research and training grants from the National Institute on Aging", add -- under Grant Nos. AG11658 and AG24399 --

Signed and Sealed this
Eighth Day of March, 2011

David J. Kappos
*Director of the United States Patent and Trademark Office*